(12) United States Patent
Arita et al.

(10) Patent No.: US 9,320,439 B2
(45) Date of Patent: Apr. 26, 2016

(54) OPHTHALMOLOGICAL IMAGE ANALYZER AND OPHTHALMOLOGICAL IMAGE ANALYSIS METHOD

(75) Inventors: Reiko Arita, Tokyo (JP); Jun Suehiro, Tokyo (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 330 days.

(21) Appl. No.: 14/008,814

(22) PCT Filed: Feb. 17, 2012

(86) PCT No.: PCT/JP2012/053779
§ 371 (c)(1),
(2), (4) Date: Sep. 30, 2013

(87) PCT Pub. No.: WO2012/137545
PCT Pub. Date: Oct. 11, 2012

(65) Prior Publication Data
US 2015/0141837 A1 May 21, 2015

(30) Foreign Application Priority Data
Apr. 8, 2011 (JP) .................................. 2011-086383

(51) Int. Cl.
*G06K 9/00* (2006.01)
*A61B 5/00* (2006.01)
(Continued)

(52) U.S. Cl.
CPC ............. *A61B 5/0077* (2013.01); *A61B 3/0025* (2013.01); *A61B 5/4887* (2013.01); *G06T 7/0012* (2013.01); *G06T 2207/30041* (2013.01)

(58) Field of Classification Search
CPC .. A61B 5/0077; A61B 3/0025; A61B 5/4887; G06T 7/0012; G06T 2207/30041
See application file for complete search history.

(56) References Cited

U.S. PATENT DOCUMENTS

| | | | |
|---|---|---|---|
| 7,976,573 B2 * | 7/2011 | Korb .......................... | A61F 7/12 128/898 |
| 2008/0081999 A1 * | 4/2008 | Gravely ................... | A61B 3/10 600/473 |
| 2011/0273550 A1 | 11/2011 | Amano et al. | |

FOREIGN PATENT DOCUMENTS

| | | |
|---|---|---|
| JP | 2007-215950 A | 8/2007 |
| JP | 2009-285447 A | 12/2009 |

OTHER PUBLICATIONS

Extended European Search Report for EP Application No. 12768210.2, Sep. 12, 2014.

(Continued)

*Primary Examiner* — Shefali Goradia
(74) *Attorney, Agent, or Firm* — Pearne & Gordon LLP

(57) ABSTRACT

Ophthalmological image analysis techniques that can present objective information about the state of distribution of the Meibomian glands are provided. An ophthalmological image analyzer 1 comprises a designator 22, an extractor 23 and a calculator 24. The designator 22 is configured to designate an area A to be analyzed in a photographed image I of an eyelid of an eye. The extractor 23 is configured to extract Meibomian-gland subareas B that represent Meibomian glands in the eyelid, on the basis of the luminance value of each pixel in the area A being analyzed which is designated by the designator 22. The calculator 24 is configured to acquire distribution information of Meibomian glands in the area A being analyzed, on the basis of the Meibomian-gland subareas B.

4 Claims, 16 Drawing Sheets

(51) Int. Cl.
*A61B 3/00* (2006.01)
*G06T 7/00* (2006.01)

(56) References Cited

OTHER PUBLICATIONS

Osama M.A. Ibrahim et al., "The Efficacy, Sensitivity, and Specificity of In Vivo Laser Confocal Microscopy in the Diagnosis of Meibomian Gland Dysfunction", In: Ophthalmology, vol. 117, No. 4, Apr. 1, 2010, pp. 665-672.

Arita R et al., "Noncontact Infrared Meibography to Document Age-Related Changes of the Meibomian Glands in a Normal Population", In: Ophthalmology, vol. 115, No. 5, May 1, 2008, pp. 911-915.
Reiko Arita (Ito Iin), Shiro Amano (Todai Daigakuin Igaku Kenkyuka Gankagaku), "Dry Eye no Atarashii Kensaho Meibom is My Boom !-Hisesshokugata Meibography no Kaihatsu-", Front Dry Eye, vol. 3, No. 2, Dec. 15, 2008, pp. 119 to 124.
Aoi Komuro, Norihiko Yokoi (Kyoto-Fu Idai Daigakuin Igaku Kenkyuka Shikaku Kino Saisei Gekagaku), "I Zenganbu Kensa Sochi 11. Instruments for meibomian gland examination", Ganka, vol. 49, No. 10, Sep. 30, 2007, pp. 1331 to 1339.
International Search Report for PCT/JP2012/053779 dated Mar. 27, 2012.

* cited by examiner

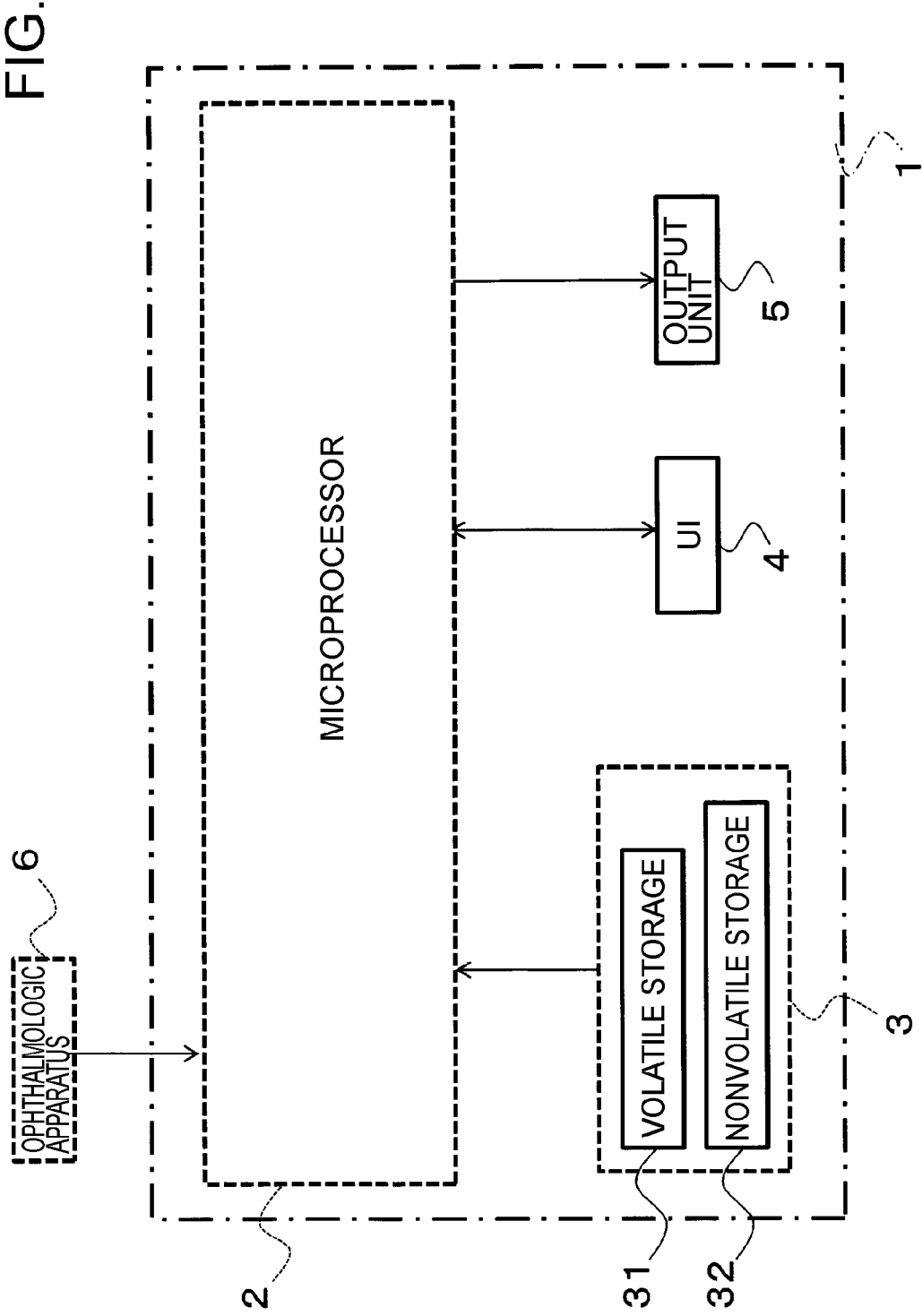

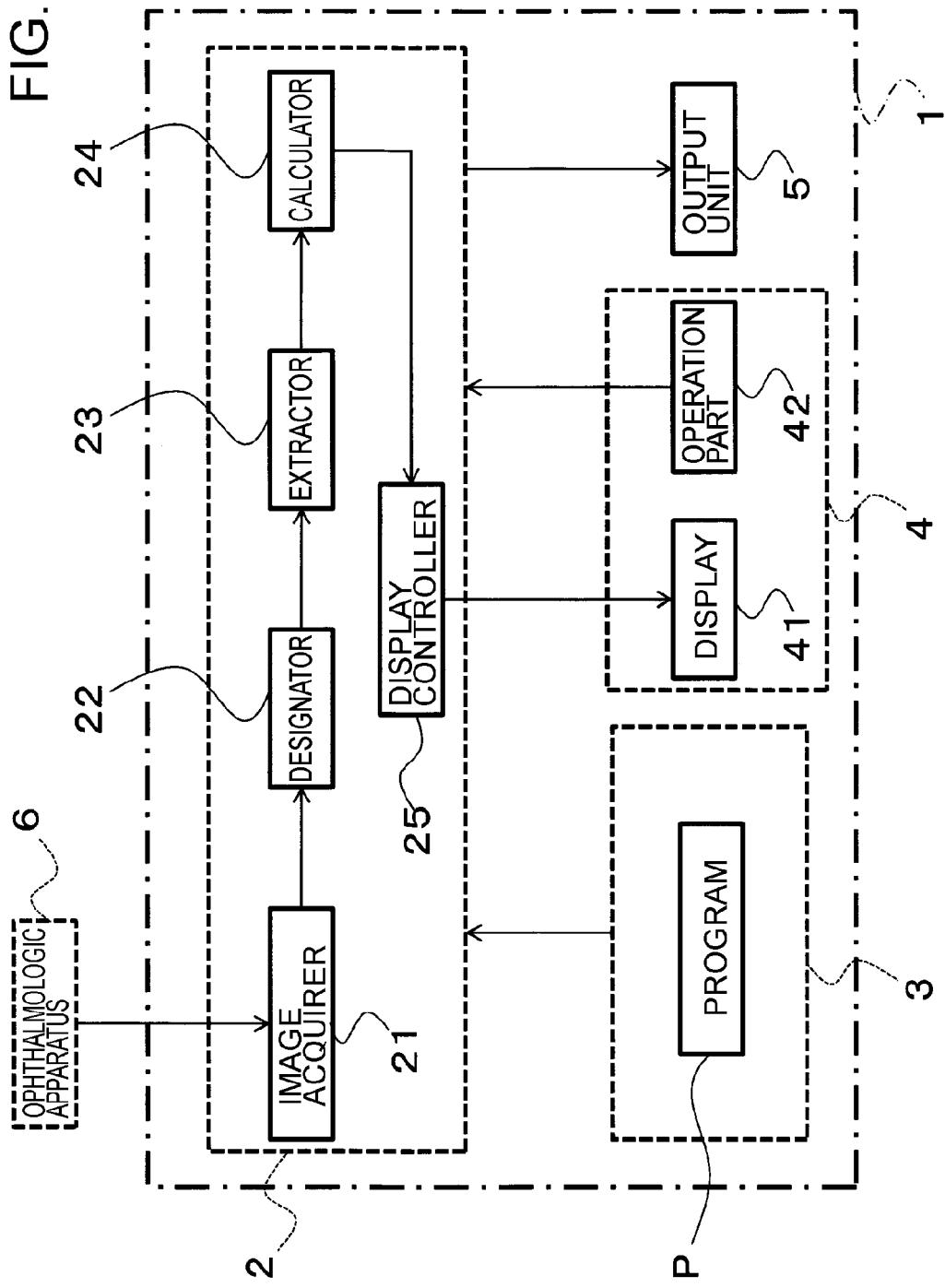

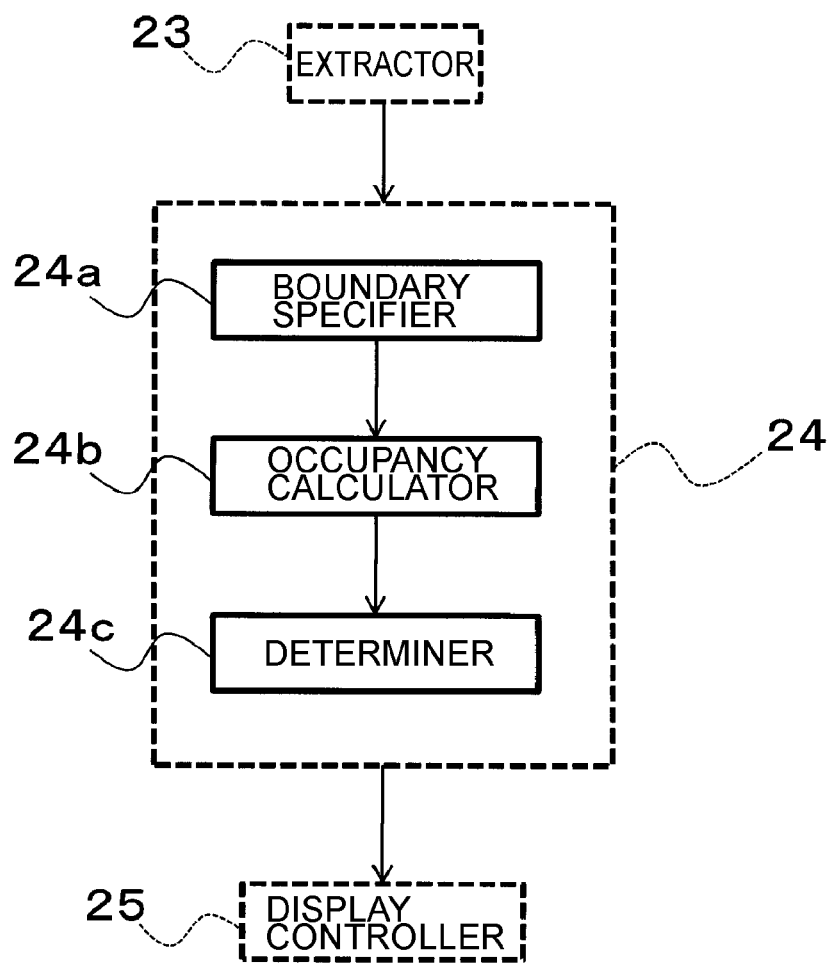

OPHTHALMOLOGICAL IMAGE ANALYZER AND OPHTHALMOLOGICAL IMAGE ANALYSIS METHOD

TECHNICAL FIELD

The present invention relates to an ophthalmological image analyzer and an ophthalmological image analysis method that are used for analysis of photographed palpebral images of the eye.

BACKGROUND ART

Dry eye is a chronic disease that affects tears and the keratoconjunctive epithelium. Causes of dry eye can be classified into the following types: "reduced tear type", which is represented by Sjogren's syndrome, and "rapid evaporation type", which is representative by Meibomian gland dysfunction (hereinafter also referred to as "MGD"). In other words, it is useful to detect abnormality in the Meibomian glands for specifying a cause for the dry eye.

The Meibomian glands are sebaceous glands located in the eyelids. The Meibomian glands supply sebum (oily substance), which creates oil layers over the surface of tears, preventing excessive evaporation of tears. The Meibomian glands exist from 20 to 30 in number in each of the upper and lower eyelids.

Technique for observing the morphology of the Meibomian glands is known as meibography. Conventionally practiced meibography has been a method of observing the structure of the Meibomian glands by illuminating them through the skin. It is, however, an invasive examination because the probe used for emitting light touches directly the eyelid, causing the subject to feel a strong unpleasantness. In addition, because the tip of the probe is thin and only capable of illuminating a narrow area, it is not easy to observe all the Meibomian glands in the upper and lower eyelids. Furthermore, doctors are required of the mastery of handling the probe.

On the other hand, a new type of meibography device is suggested to take advantage of the light source used in a slit-lamp microscope (Refer to patent document 1). This device comprises a slit-lamp microscope that is equipped with a small-size infrared CCD camera and an infrared filter. According to this device, all the Meibomian glands in the upper and lower eyelids are readily observable with low invasiveness.

PRIOR ART DOCUMENTS

Patent Documents

[Patent document 1] Japanese Laid-Open Patent Publication No. 2009-285447

SUMMARY OF THE INVENTION

Problems to be Solved by the Invention

Here, it is possible to make a diagnosis of MGD on the basis of the state of distribution of the Meibomian glands (ratio of the Meibomian glands occupying the eyelid, shapes of the Meibomian glands, etc.), which have been detected by meibography.

However, it has been common that examiners make diagnoses subjectively on the state of distribution of the Meibomian glands observed by meibography. As a result, there has been a problem that different diagnoses can result depending on the degree of mastery of the examiner.

The present invention is to solve the above-mentioned problem, and the object thereof is to provide ophthalmological image analysis techniques that can present objective information about the state of distribution of the Meibomian glands.

Means for Solving the Problem

In order to achieve the above-mentioned object, an ophthalmological image analyzer according to a first embodiment comprising: a designator, an extractor and a calculator. The designator is configured to designate an area to be analyzed in a photographed image of an eyelid of an eye. The extractor is configured to extract Meibomian-gland subareas that represent Meibomian glands in the eyelid, on the basis of the luminance value of each pixel in the area being analyzed. The calculator is configured to acquire distribution information of Meibomian glands in the area being analyzed, on the basis of the Meibomian-gland subareas.

Moreover, in order to achieve the above-mentioned object, an ophthalmological image analyzer according to a second embodiment is the ophthalmological image analyzer according to the first embodiment, further comprising a storage configured to store standard information that indicates a standard state of distribution of Meibomian glands for a normal eye. The calculator comprises a determiner configured to determine the existence or nonexistence of abnormality in the Meibomian glands, on the basis of the distribution information and the standard information.

Moreover, in order to achieve the above-mentioned object, an ophthalmological image analyzer according to a third embodiment is the ophthalmological image analyzer according to the first embodiment, wherein the calculator comprises a boundary specifier and an occupancy calculator. The boundary specifier is configured to specify vertices for the Meibomian-gland subareas, and on the basis of the vertices, specify a boundary that divides the area being analyzed into the Meibomian-gland subareas with the inter-Meibomian gland subareas, which are subareas that exist between the Meibomian-gland subareas, and into the other remaining external subareas. The occupancy calculator is configured to divide the sum of the surface area of the Meibomian-gland subareas and the surface area of the inter-Meibomian gland subareas by the surface area of the area being analyzed, calculating the quotient, which represents occupancy ratio as the distribution information. It should be noted that the invention according to the third embodiment can be applied to the invention according to the second embodiment.

Moreover, in order to achieve the above-mentioned object, an ophthalmological image analyzer according to a fourth embodiment is the ophthalmological image analyzer according to the first embodiment, wherein the calculator comprises a boundary specifier configured to specify vertices for the Meibomian-gland subareas, and on the basis of the vertices, specify a boundary that divides the area being analyzed into the Meibomian-gland subareas with the inter-Meibomian gland subareas, which are subareas that exist between the Meibomian-gland subareas, and into the other remaining external subareas. The calculator acquires, as the distribution information, shape information that indicates the shape of the boundary. It should be noted that the invention according to the fourth embodiment can be applied to the invention according to the second embodiment.

Moreover, in order to achieve the above-mentioned object, an ophthalmological image analyzer according to a fifth embodiment is the ophthalmological image analyzer according to the first embodiment, wherein the calculator acquires, as the distribution information, a degree of bending for the Meibomian glands, on the basis of the shape of the Meibomian-gland subareas. It should be noted that the invention according to a fifth embodiment can be applied to the invention according to the second embodiment.

Moreover, in order to achieve the above-mentioned object, an ophthalmological image analyzer according to a sixth embodiment is the ophthalmological image analyzer according to the first embodiment, further comprising a storage configured to store a predetermined threshold value and a standard occupancy ratio, which is the ratio of Meibomian-gland subareas and inter-Meibomian gland subareas, which are subareas that exist between the Meibomian-gland subareas, occupying an area being analyzed of a normal eye. The calculator comprises a boundary specifier, an occupancy calculator, a falloff-degree calculator and a determiner. The boundary specifier is configured to specify vertices for the Meibomian-gland subareas, and on the basis of the vertices, specify a boundary that divides the area being analyzed into the Meibomian-gland subareas with the inter-Meibomian gland subareas, which are subareas that exist between the Meibomian-gland subareas, and into the other remaining external subareas. The occupancy calculator is configured to divide the sum of the surface area of the Meibomian-gland subareas and the surface area of the inter-Meibomian gland subareas by the surface area of the area being analyzed, calculating the quotient, which represents occupancy ratio. The falloff-degree calculator is configured to acquire, as the distribution information, a degree of falling off of the Meibomian glands compared with the normal eye by calculating the difference between the occupancy ratio and the standard occupancy ratio. The determiner is configured to determine the existence or nonexistence of abnormality in the Meibomian glands, on the basis of the degree of falling off and the threshold value.

Moreover, in order to achieve the above-mentioned object, an ophthalmological image analyzer according to a seventh embodiment is the ophthalmological image analyzer according to the sixth embodiment, wherein the calculator further comprises a bending-degree calculator and a cause specifier. The bending-degree calculator is configured to acquire, as the distribution information, a degree of bending of the Meibomian glands on the basis of the shape of the Meibomian-gland subareas which are extracted by the extractor. The cause specifier is configured to specify, when the determiner determines that there is an abnormality in the Meibomian glands, a possible cause for the abnormality in the Meibomian glands on the basis of shape information that indicates the shape of the boundary which is specified by the boundary specifier, and/or of the degree of bending.

Moreover, in order to achieve the above-mentioned object, an ophthalmological image analyzer according to an eighth embodiment is the ophthalmological image analyzer according to the first embodiment, further comprising a display and a display controller configured to display the photographed image and a processed image side by side on the display, the processed image showing the Meibomian-gland subareas which are extracted by the extractor. It should be noted that the invention according to the eighth embodiment can be applied to the invention according to any of the above embodiments.

Moreover, in order to achieve the above-mentioned object, an ophthalmological image analyzer according to a ninth embodiment is the ophthalmological image analyzer according to the eighth embodiment, wherein the display controller displays the distribution information, the photographed image, and the processed image side by side.

Moreover, in order to achieve the above-mentioned object, an ophthalmological image analyzer according to a tenth embodiment is the ophthalmological image analyzer according to the eighth embodiment, further comprising an operation part. When an instruction is given to one of the photographed image and the processed image by using the operation part, the display controller reflects the result of the instruction onto the other of the photographed image and the processed image. It should be noted that the invention according to the tenth embodiment can be applied to the invention according to the ninth embodiment.

Moreover, in order to achieve the above-mentioned object, a ophthalmological image analysis method according to an eleventh embodiment comprises the following steps: a step of designating an area to be analyzed in a photographed image of an eyelid of an eye; a step of extracting Meibomian-gland subareas that represent Meibomian glands in the eyelid, on the basis of the luminance value of each pixel in the area being analyzed; and a step of acquiring distribution information of Meibomian glands in the area being analyzed, on the basis of the Meibomian-gland subareas. It should be noted that a method realized by any of the inventions according to any of the above embodiments can be incorporated with the ophthalmological image analysis method according to the eleventh embodiment.

Effects of the Invention

The ophthalmological image analyzer according to the present invention functions to obtain information about the distribution of the Meibomian glands by analyzing a photographed palpebral image. As a result, it is possible to provide objective information about the state of distribution of the Meibomian glands without subjective influence from the examiner or the like.

BRIEF DESCRIPTION OF THE DRAWINGS

FIG. 1A is a block diagram illustrating a hardware configuration of the ophthalmological image analyzer according to the first embodiment.

FIG. 1B is a block diagram illustrating a software configuration of the ophthalmological image analyzer according to the first embodiment.

FIG. 2 is a block diagram illustrating a configuration of the calculator in the ophthalmological image analyzer according to the first embodiment.

EMBODIMENTS FOR CARRYING OUT THE INVENTION

First Embodiment

Figure 3:
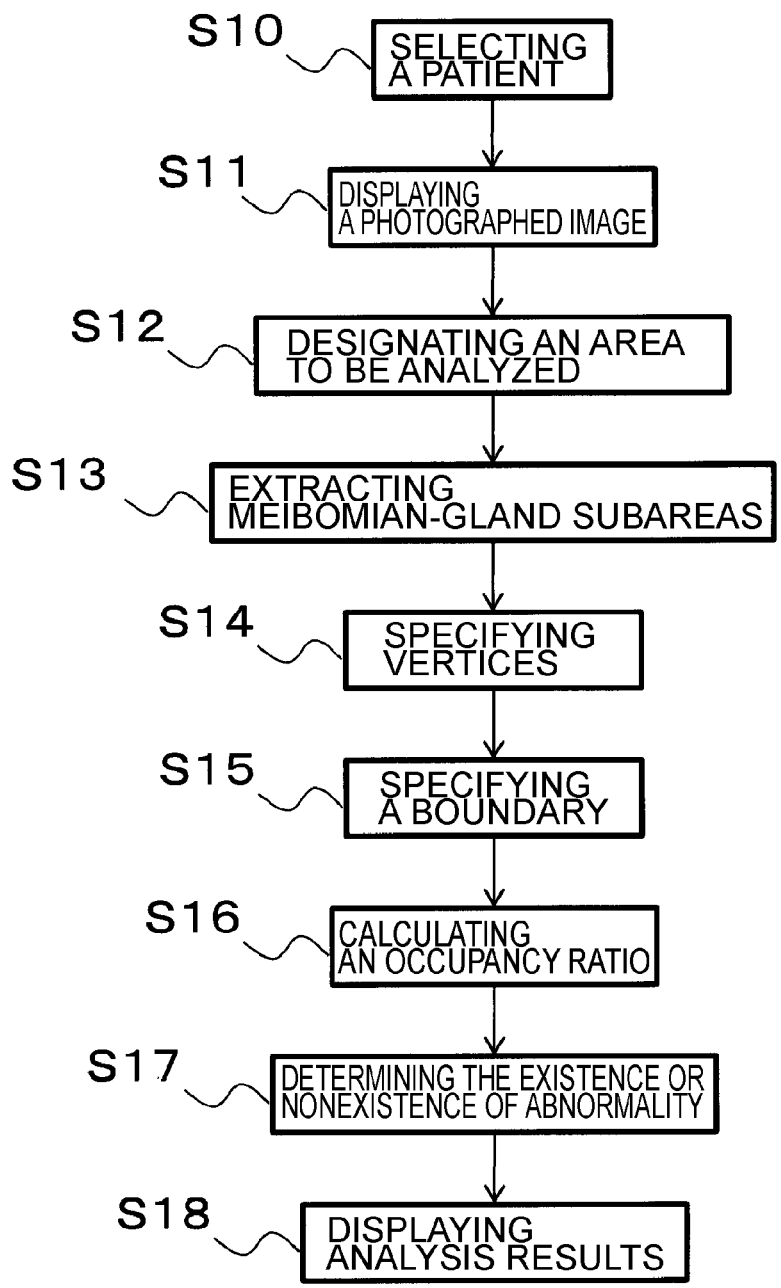
FIG. 3 is a flowchart illustrating an action of the ophthalmological image analyzer according to the first embodiment.

Now, an example of an ophthalmological image analyzer 1 according to a first embodiment is described with reference to FIG. 1A through FIG. 10. It should be noted that since the terms "image" and "image data" correspond to each other one-on-one, they may be used as identical terms in the present specification.

<Configuration of the Apparatus>

The configuration of the ophthalmological image analyzer 1 is described with reference to FIG. 1A through FIG. 3. The ophthalmological image analyzer 1 is configured to include, for example, a general-purpose computer. The ophthalmological image analyzer 1 is configured to include a microprocessor 2, a storage 3, a UI (User Interface) 4, and an output unit 5.

The microprocessor 2 comprises an arbitrary microprocessor such as a CPU (Central Processing Unit) or an MPU (Micro Processing Unit), which is used for execution of various computational processes and control processes based on a predetermined program P.

The storage 3 is configured to include a volatile storage 31 and a nonvolatile storage 32.

The volatile storage 31 comprises, for example, an RAM (Random Access Memory), where the program and data being dealt with by the microprocessor 2 are loaded.

The nonvolatile storage 32 is configured to include such storage devices as a HDD (Hard Disk Drive) and ROM (Read Only Memory). The nonvolatile storage 32 stores the above-mentioned predetermined program P in advance The microprocessor 2 loads the program P on the volatile storage 31 (RAM), thereby causing the ophthalmological image analyzer 1 to execute the characteristic processes of this embodiment. In addition, the nonvolatile storage 32 (particularly the hard disk drive) stores, for example, the results of the analysis done by the ophthalmological image analyzer 1 and the image data that are acquired by an ophthalmologic apparatus 6. The image data stored in the nonvolatile storage 32 are, however, not restricted to the image data acquired through the ophthalmologic apparatus 6. For example, it is possible to receive data of a previously photographed image that is stored in an external storage via a network, and to store the data together with a patient ID into the nonvolatile storage 32.

The ophthalmologic apparatus 6 can be, for example, a Meibomian gland observation device (meibography) that comprises a slit lamp equipped with an infrared light source and a visible light cut filter (refer, for example, to patent document 1). photographing the eyelid of the eye by using meibography enables observation of the morphology of the Meibomian glands in the eyelid.

The user interface 4 is configured to include a display 41 and an operation part 42.

The display 41 comprises an arbitrary displaying device like an LCD (Liquid Crystal Display) or CRT (Cathode Ray Tube) display.

The operation part 42 is used as operation device for inputting various instructions to the ophthalmological image analyzer 1 and for inputting information about an image displayed on the display 41. The operation part 42 comprises, for example, a key-board, a mouse, a track ball, a joystick, etc. In addition, a GUI (Graphical User Interface) displayed on the display 41 can be also used as the operation part 42.

The output unit 5 outputs results of the analysis done by the ophthalmological image analyzer 1 to an external device. The output unit 5 comprises, for example, a printer, which prints analysis results on paper, as an output. Alternatively, the output unit 5 may include a recording device that records analysis results on recording media. The recording media may include any of optical discs, magneto-optical discs (CD-ROM, DVD-RAM, DVD-ROM, MO, etc.), and magnetic media (Floppy (registered trademark) disks, ZIPs, etc). In addition, the output unit 5 may include a communication interface (LAN card, etc.), that is configured to output analysis results via a network (LAN, etc.).

<Configuration of the Microprocessor>

The microprocessor 2 in this embodiment functions as an image acquirer 21, a designator 22, an extractor 23, a calculator 24, and a display controller 25 based on the programs stored in the storage 3.

[Image Acquirer]

The image acquirer 21 acquires a photographed palpebral image (image data) of an eye through the interface from the ophthalmologic apparatus 6 or the storage 3 in accordance with the input from the operation part 42. The photographed image acquired is displayed on the display 41. The "photographed image" here is an image obtained by illuminating the eyelid (the rear side of the eyelid) with infrared light and capturing reflected light thereof. A plurality of Meibomian glands exist in the eyelid. Therefore, the "photographed image" is an image that pictures a predetermined area of the eyelid, which includes Meibomian glands (i.e., sebum in Meibomian glands). It should be noted that the "photographed image" may be any image from which the morphology of the Meibomian glands is observable. Accordingly, the light used for the image capturing is not limited to infrared light.

[Designator]

The designator 22 designates an area to be analyzed of the photographed image. The term "area to be analyzed" is a predetermined area of the eyelid of the eye, and shows a region from which the extractor 23 extracts information of Meibomian glands. Accordingly, the "area to be analyzed" should include at least a part of a plurality of Meibomian glands. In other words, the area may be the entirety of the eyelid or may be part of the eyelid.

It is possible to apply a configuration in which the specification of the area to be analyzed by using the designator 22 is automatically executed, or a configuration in which it is manually executed.

In the case that the specification of the area to be analyzed is automatically executed, it is executed, for example, based on the pixel values of the photographed image. The following is an example of this case.

In the case where the whole area of the eyelid is designated as the area to be analyzed, for example, the designator 22 specifies the periphery of an image area that corresponds to the rear side of the eyelid in the photographed image, on the basis of the luminance value of each pixel. The peripheral area includes a first boundary region corresponding to the boundary between the rear side of the eyelid and the eye and a second boundary region corresponding to the boundary between the rear side of the eyelid and the epidermis of the face. The first boundary region is determined, for example, on the basis of differences between pixel values in an image area corresponding to the rear side of the eyelid and pixel values in an image area corresponding to the cornea and the sclera. The second boundary region is determined, for example, on the basis of differences between pixel values in an image area corresponding to the rear side of the eyelid and pixel values in an image area corresponding to the epidermis of the face. Alternatively, it is possible to specify an image area corresponding to the eyelashes in the photographed image, specify, from this image area, the positions corresponding to the borders of the eyelashes, and determine the second boundary region on the basis of the specified positions. The designator 22 designates, as an area to be analyzed, the area surrounded by the peripheral area which is specified in this way.

Furthermore, in the case where an area that corresponds to a part of the eyelid is designated as an area to be analyzed, the designator 22 designates, as an area to be analyzed, for example, a part that has higher luminance values than the other remaining part of the whole area of the eyelid, i.e., an area that more likely includes Meibomian glands.

In the case where the specification of the area to be analyzed is executed manually, for example, the examiner specifies a desired area on the photographed image displayed on the display 41. The following is an example of this case.

In the case where the whole area of the eyelid is specified as an area to be analyzed, the examiner draws a periphery of the eyelid over the photographed image displayed on the display 41 by using the operation part 42. The designator 22 then specifies the area surrounded by the periphery as an area to be analyzed.

On the other hand, in the case where an area that corresponds to a part of the eyelid is specified as an area to be analyzed, the examiner draws a line to surround a desirable part of the palpebral area over the photographed image displayed on the display 41 by using the operation part 42. The designator 22 then specifies the area surrounded by the drawn line as an area to be analyzed.

Instead, the specification of the area to be analyzed can be executed semiautomatically. For example, the storage 3 or the like can store, in advance, multiple sets of data that indicate areas to be analyzed in correspondence with patient information (age, sex, etc.) (each set of data corresponding to a "predetermined area"). In this case, when the examiner inputs patient information by using the operation part 42, the designator 22 reads out from the storage 3 a set of data that indicates a corresponding area to be analyzed, and then executes a correction process of the data based on the magnification of the photographed image. Then, the designator 22 draws an area to be analyzed based of the corrected data over the photographed image displayed on the display 41. The patient information may be automatically acquired from his/her electronic medical record. In addition, it is possible to store the data indicating areas to be analyzed in relation to the patient information and photographic conditions (photographic magnification, etc.). it should be noted that, generally, two technical cases are possible: one is the case in which the area to be analyzed that has been designated automatically is corrected manually; and the other is the case in which the area to be analyzed that has been drawn manually is corrected automatically.

[Extractor]

The extractor 23 extracts a Meibomian-gland subarea on the basis of the luminance value of each pixel in the area to be analyzed. The term "Meibomian-gland subarea" means a part that corresponds to a Meibomian gland in the predetermined palpebral area (i.e., the area to be analyzed).

The Meibomian-gland subareas are extracted, for example, by technique of region segmentation. That is, the extractor 23, at first, obtains the luminance value of each pixel in the area being analyzed in the photographed image. The extractor 23, then, determines whether or not the luminance value of each pixel is equal to or greater than a threshold value, and extracts the parts whose luminance values are equal to or greater than the threshold value as Meibomian-gland subareas. The threshold value is a determinant of whether the luminance value of a certain pixel indicates part of a Meibomian gland or part of other subareas. The threshold value may be a value that has been determined clinically from photographed images, etc. It is desirable that the threshold value includes a statistical value like a mean, a median, a mode, or a standard deviation. The threshold value is stored in advance as a constant value in the storage 3 or can be specified for each of the photographed images from which Meibomian-gland subareas are extracted, by using the operation part 42. Incidentally, the luminance values of photographed images vary depending on photographic conditions. It is, therefore, preferable that the threshold value is adjusted in correspondence with photographic conditions. Alternatively, it is also possible adjust the luminance values of the photographed image in correspondence with its photographic conditions.

The method used for the extraction of Meibomian-gland subareas is not restricted to the above-mentioned techniques. Any known image-processing methods, such as filtering and region-glowing, can be applied. In addition, such preprocessing as contrast-enhancing or shaming may be applied before the extraction of Meibomian-gland subareas.

[Calculator]

The calculator 24 acquires distribution information of Meibomian glands in the area being analyzed, on the basis of the Meibomian-gland subareas extracted by the extractor 23. The "distribution information" is information about the state of distribution of Meibomian glands in the palpebra (e.g., the ratio of the Meibomian glands occupying the palpebra, the shapes of the Meibomian glands, etc.).

The calculator 24 in this embodiment is configured to include a boundary specifier 24a, an occupancy calculator 24b, and a determiner 24c.

(Boundary Specifier)

The boundary specifier 24a specifies vertices for the Meibomian-gland subareas, and then, based on the vertices, defines boundaries which segment the Meibomian-gland subareas with their inter-Meibomian gland subareas and the other remaining area (hereinafter also referred to as "external subareas") in the area being analyzed. The term "inter-Meibomian gland subarea" represents a part that is surrounded by the line passing the vertex of each of the Meibomian glands and by the Meibomian-gland subareas in the area being analyzed. The term "vertex" means the point that indicates the end (tip) of a Meibomian gland. For example, if the upper eyelid is being examined with the eyelid being turned over, the vertices are located lowermost. The term "external subarea" represents the area which is sectioned out by the line passing the vertex of each of the Meibomian glands and in which no Meibomian-gland subarea exists. Thus, the inter-Meibomian gland subareas and the external subarea are specified by defining the line that passes the vertices of the Meibomian-gland subareas (hereinafter also referred to as "boundary line").

Figure 4:
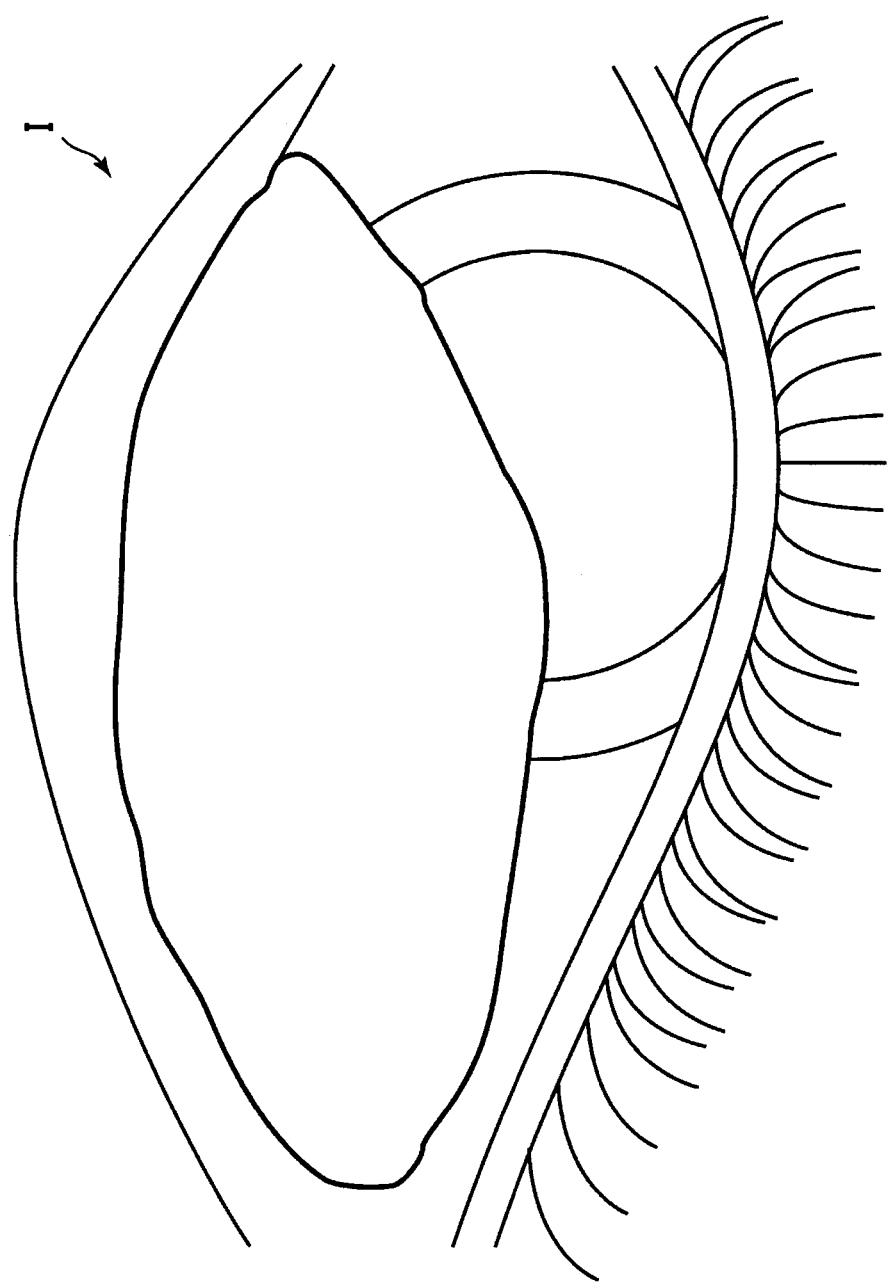
FIG. 4 is a diagram supplementing the explanation of the flowchart according to the first embodiment.

The following is an example of method for specifying the vertices of the Meibomian-gland subareas. In the following description, one direction (e.g., direction connecting the inner and outer corners of the eye, i.e., the horizontally extending direction in FIG. 4) of the eye is defined as x-axis, and the direction perpendicular to this direction is defined as y-axis. FIG. 4 represents a photographed image of a right eye, so the inner corner side of the eye is in the +x direction, and the upper eyelid side is in the +y direction. It should be noted that the x-y coordinate system can be arbitrarily defined. For example, the horizontal direction of the frame of a photographed image of an eye can be defined as x-axis direction while the vertical direction of the frame can be defined as y-axis direction.

A plurality of Meibomian-gland subareas exist in a photographed image. For each of the Meibomian-gland subareas in the photographed image, the boundary specifier 24a derives a curve (a function) y=f(x) that reflects the shape of the Meibomian-gland subarea, and analyzes the shape to determine its vertex.

Such a curve (a function), y=f(x), may be a curve that indicates the periphery of the Meibomian-gland subarea, or a curve that is obtained by thinning the Meibomian-gland subarea. The following description concerns a curve that indicates the periphery of the Meibomian-gland subarea.

For calculation of a vertex on a curve (function), y=f(x), there is, for example, a method of differentiating the function f(x). As a method that uses differentiation, there is a method that applies the second order differential of the function f. Specifically, the function f(x) is twice differentiated (f'(x)), and then, calculations are made to achieve the values of x and y that realize f'(x)=0 (inflection point).

The boundary specifier 24a specifies the coordinate values of the inflection points in the photographed image as vertices. If there are multiple inflection points for one Meibomian gland, then the boundary specifier 24a specifies one of the points as a vertex. For example, when a photographed image of an upper eyelid is concerned, the boundary specifier 24a specifies, as vertex, the inflection point whose y coordinate is the least among the inflection points (i.e., the inflection point that is located lowermost in the frame of the photographed image, or the inflection point of the Meibomian gland that is the nearest to the lower eyelid).

It should be noted that, instead of calculating the curve that indicates the periphery as described previously, the boundary specifier 24a can execute thinning of the Meibomian-gland subareas, thereby obtaining a curve that approximates the shape of each of the Meibomian-gland subareas. In this case, the boundary specifier 24a specifies, as vertex, the point whose y coordinate is the least in the curve which have been achieved by thinning (in the case of the upper eyelid).

Based on the specified vertices of the Meibomian glands, the boundary specifier 24a calculates a boundary line. The boundary line may be expressed, for example, as a spline curve or a Bezier curve passing the vertices. Then, on the basis of the boundary line and the extraction result of the Meibomian-gland subareas, the boundary specifier 24a defines boundaries that partition the area being analyzed into the Meibomian-gland subareas, the inter-Meibomian gland subareas, and the external subareas.

(Occupancy Calculator)

The occupancy calculator 24b divides the sum of the surface area of the Meibomian-gland subareas and the surface area of the inter-Meibomian gland subareas by the surface area of the area being analyzed, thereby obtaining the quotient as occupancy ratio.

The term "occupancy ratio" is a value that indicates the proportion of the Meibomian-gland subareas and the inter-Meibomian gland subareas to the area being analyzed, and it is an example of the state of distribution of the Meibomian glands. For example, if abnormalities in the Meibomian glands are caused by wearing of a contact lens, then it is often a case in which each of the Meibomian glands is shortened as a whole. In this case, the occupancy ratio is lower than that of the normal (healthy) eye (described later as "standard occupancy ratio"). In other words, based on the occupancy ratio, it is possible to make a determination of the existence of abnormality in the Meibomian glands and, if there is, the causes of the abnormality. In this embodiment, the "occupancy ratio" is considered as "distribution information".

The following describes an example of a method of calculating the occupancy ratio. For each of the Meibomian-gland subareas, the inter-Meibomian gland subareas and the external subareas, the occupancy calculator 24b obtains the number of pixels included in the concerned subarea. The occupancy calculator 24b, then, calculates the surface area for each of the subareas, by multiplying the number of pixels in each subarea by the unit area of the pixel, and then by dividing this product by the value of the photographic magnification which was applied when the image was obtained. After that, the occupancy calculator 24b calculates the sum of the surface area of the Meibomian-gland subareas and the surface area of the inter-Meibomian gland subareas, and then calculates the occupancy ratio by dividing the sum by the surface area of the area being analyzed. The value of the photographic magnification applied for the acquisition of the photographed image and the unit surface area of the pixel are stored, for example, in the storage 3.

(Determiner)

The determiner 24c determines the existence or nonexistence of abnormality in the Meibomian glands on the basis of the distribution information and standard information. The expression "to determine the existence or nonexistence of abnormality" means the determination of whether the distribution information is within the range of standard information. For example, if the determination results in that the distribution information is within the range of standard information, the determiner 24c determines that the Meibomian glands are normal (there is no abnormality). On the other hand, if the determination results in that the distribution information is out of the range of standard information, then the determiner 24c determines that the Meibomian glands have abnormality. Instead, the determiner 24c may determine whether it is larger or smaller than that the standard information.

The term "standard information" is information that indicates a standard state of distribution of the Meibomian glands in normal eyes. The standard state of distribution is, for example, obtained statistically from photographic data of normal eyes of a number of people. The standard information is stored, for example, in the storage 3. In this embodiment, the "standard information" is defined as standard occupancy ratio that is a standard proportion in occupancy of the Meibomian-gland subareas and the inter-Meibomian gland subareas in the area for analysis of normal eyes. It is desirable that the standard information be a statistical value such as a mean, a median, a mode, or a standard deviation. Moreover, the standard information may be set in accordance with such patient conditions as age, sex, wearing or not of contact lenses, and existence of a related medical history. It should be noted that, conversely to this, it is also possible to determine that there is abnormality in the Meibomian glands if the distribution information is within the range of the standard information. In this case, the standard information is a value that has been obtained statistically from photographic data of diseased eyes of a number of people.

The following describes an example of a specific action of the determiner 24c. The determiner 24c reads out the standard occupancy ratio from the storage 3 and compares it with the occupancy ratio calculated by the occupancy calculator 24b. Here, if the concerned occupancy ratio is lower than the standard occupancy ratio, it means that there are fewer Meibomian-gland subareas in the area being analyzed than normal eyes. In other words, it can be understood that the Meibomian-gland subareas have decreased from the normal state. In this case, the determiner 24c determines that the Meibomian glands have some kind of abnormality. This determination result is displayed by the display controller 25 as a numerical value or a message on the display 4. Instead, the microprocessor 2 may output the determination result with the output unit 6.

[Display Controller]

Figure 10:
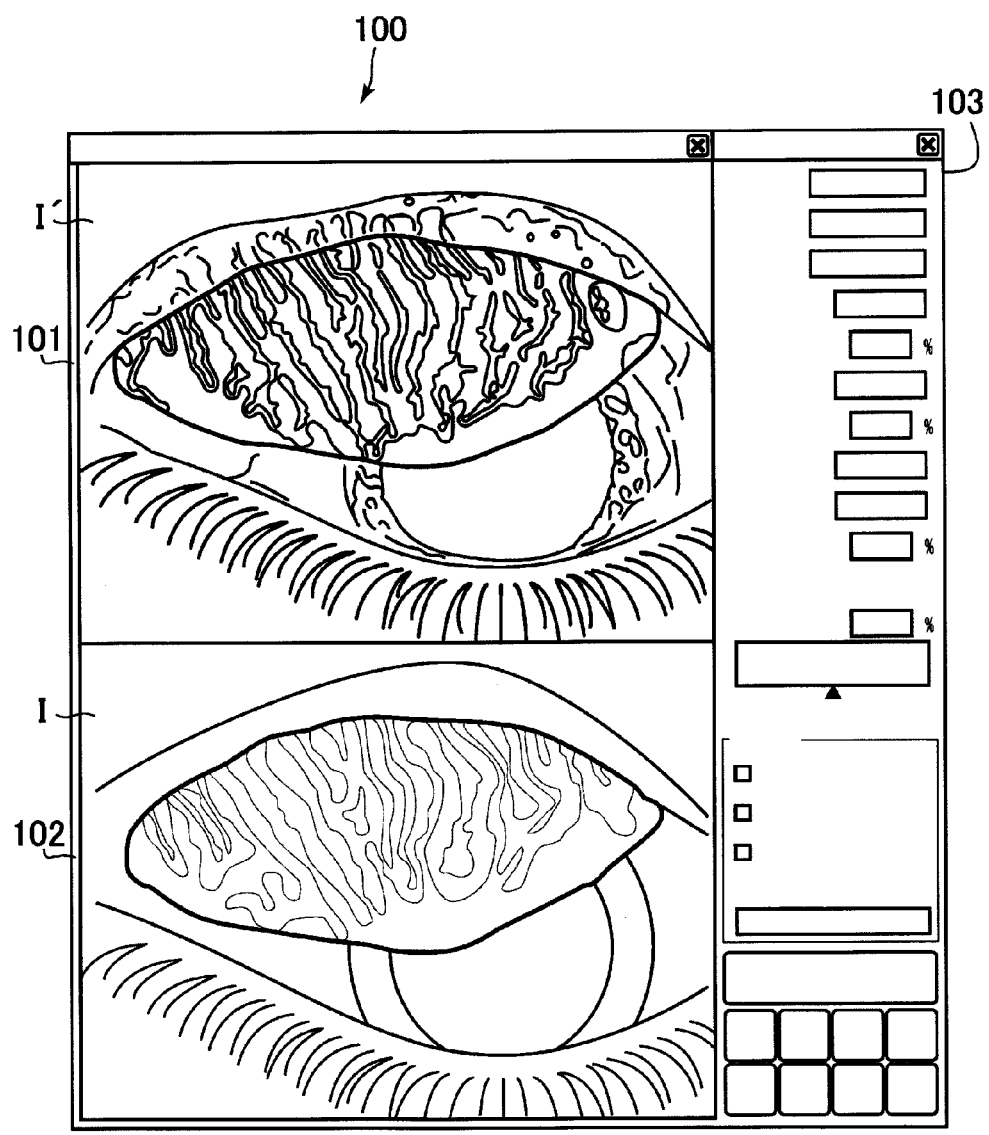
FIG. 10 is a diagram illustrating a display screen on the display in the ophthalmological image analyzer according to the first embodiment.

The display controller 25 arranges and displays the photographed image, a processed image, and distribution information on the display 4 (Refer to FIG. 10). The term "processed image" is, for example, an image that is obtained by applying an image-processing like enhancement to the photographed image for the purpose of making the Meibomian-gland subareas extracted by the extractor 23 look clear (Refer to the symbol I' in FIG. 10). The enhancement is executed, for example, by the display controller 25. On the display 41, patient information and GUI items etc. can be also displayed together with the photographed image, the processed image and the distribution information.

<Actions>

Now, actions taken by the ophthalmological image analyzer 1 according to this embodiment are described with reference to FIG. 3 through FIG. 10. FIG. 4 through FIG. 9 illustrate a photographed image of a palpebra (of the right eye) which is displayed on the display 41. FIG. 10 shows an example of displaying mode of analysis results, etc. by the ophthalmological image analyzer 1.

At first, the examiner selects a desired patient, for example, in the list of patients displayed on the display 41 by using the operation part 42 etc. (S10). The microprocessor 2 displays a list of photographed palpebral image data that correspond to the selected patient on the display 41. It should be noted that it is possible to input a patient ID with the operation part 42 in order to specify a patient corresponding to the concerned patient ID.

The examiner selects, from the list of sets of photographed image data, a photographed image I to which analysis of Meibomian-gland subareas is to be carried out. The image acquirer 21 reads out the data that correspond to the photographed image I which has been selected in S10 from the storage 3 etc. and displays it on the display 41 (S11. Refer to FIG. 4).

Figure 5:
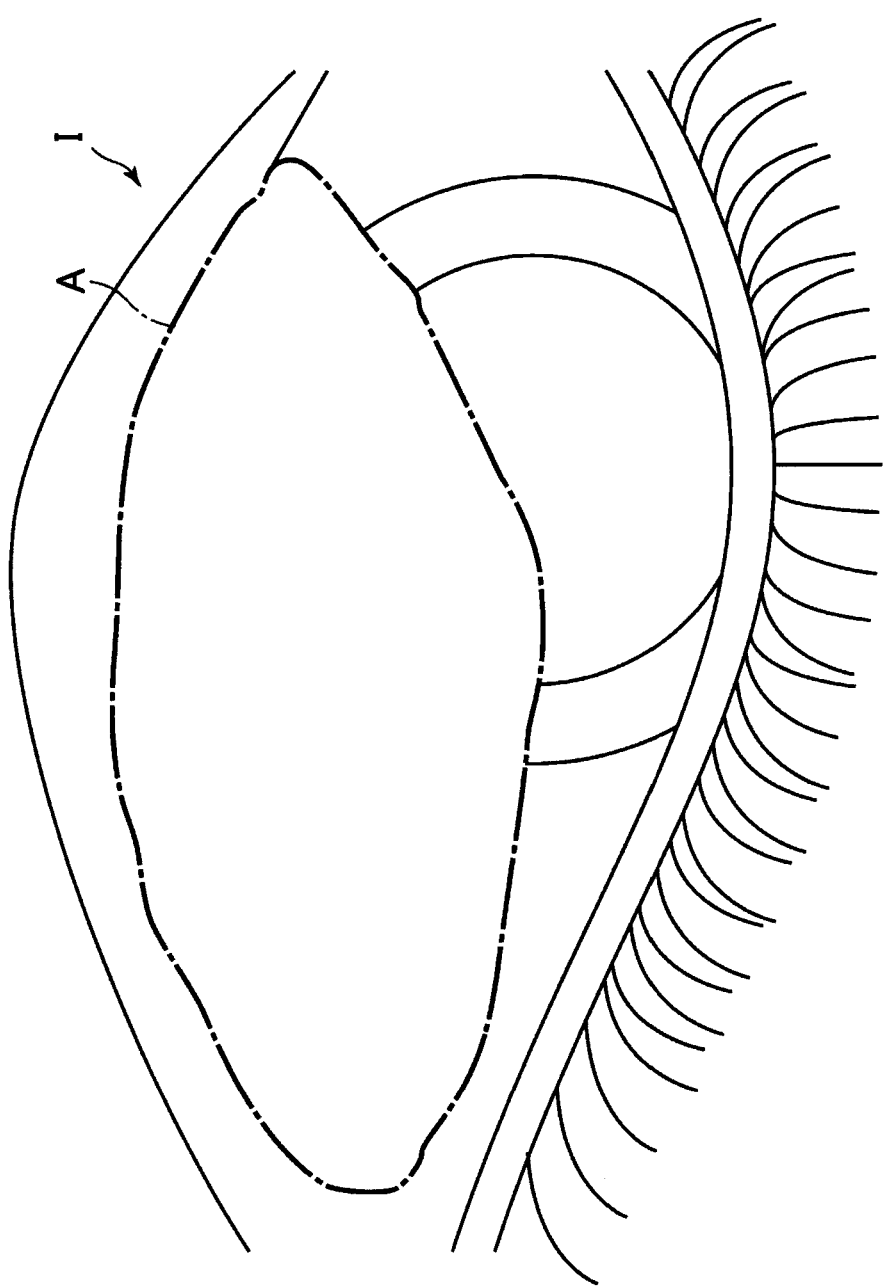
FIG. 5 is a diagram supplementing the explanation of the flowchart according to the first embodiment.

For the photographed image I which has been displayed at S11, the designator 22 designates an area to be analyzed A (S12. Refer to FIG. 5). The designation of the concerned area A is executed, for example, in a way in which the examiner uses the operation part 42 to mark a desired area in the photographed image I displayed on the display 41. Instead, it is possible that the designator 22 automatically designates the area A to be analyzed based on patient information input using the operation part 42.

Figure 6:
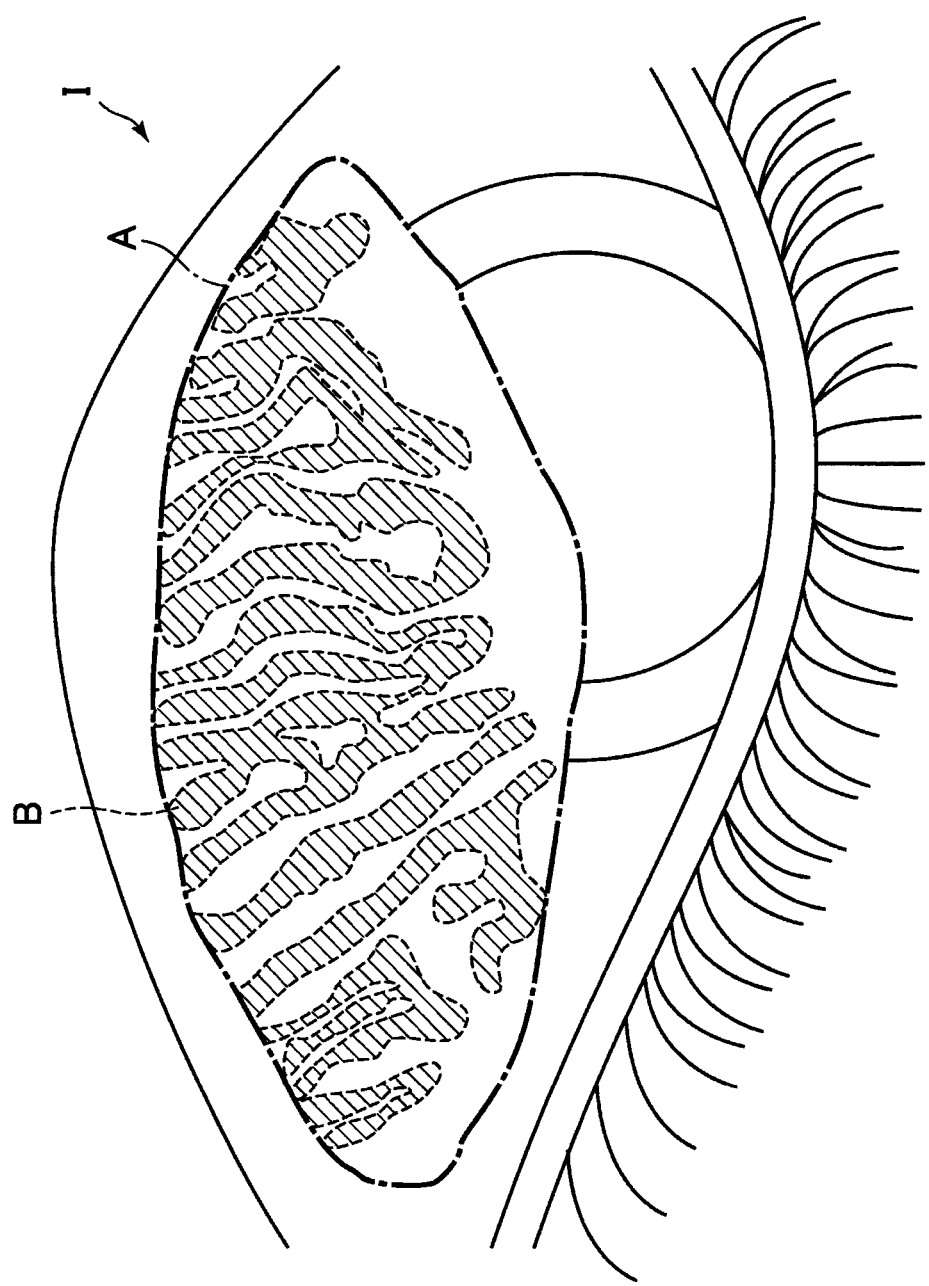
FIG. 6 is a diagram supplementing the explanation of the flowchart according to the first embodiment.

The extractor 23 extracts Meibomian-gland subareas B on the basis of the luminance value of each pixel in the area A being analyzed designated in S12 (S13. Refer to FIG. 6).

For the Meibomian-gland subareas B extracted in S13, the boundary specifier 24a specifies vertices for the Meibomian-gland subareas B (S14). Generally, the Meibomian-gland subareas exist in plurality, and therefore, the boundary specifier 24a specifies one vertex for each of the Meibomian-gland subareas.

Figure 7:
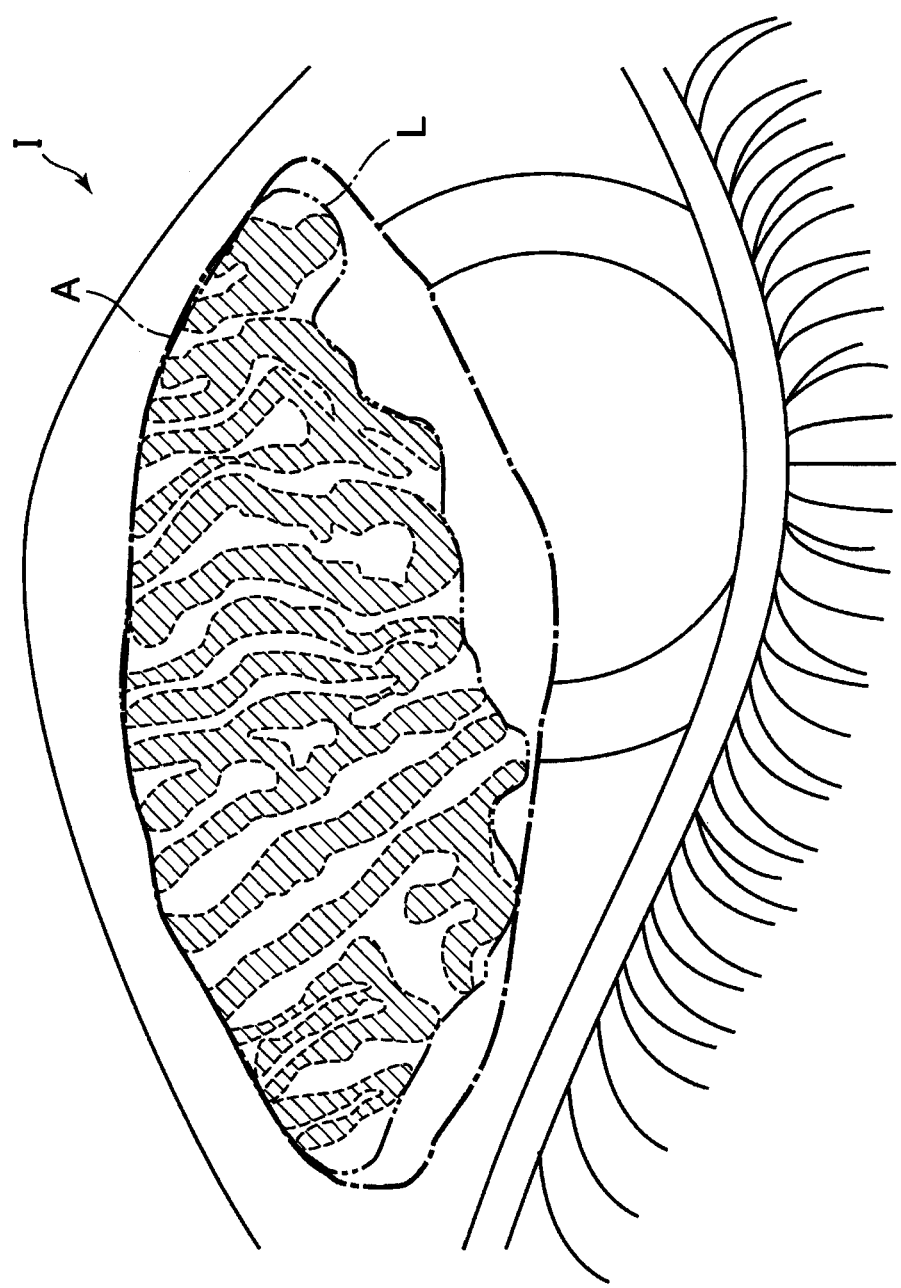
FIG. 7 is a diagram supplementing the explanation of the flowchart according to the first embodiment.
Figure 8:
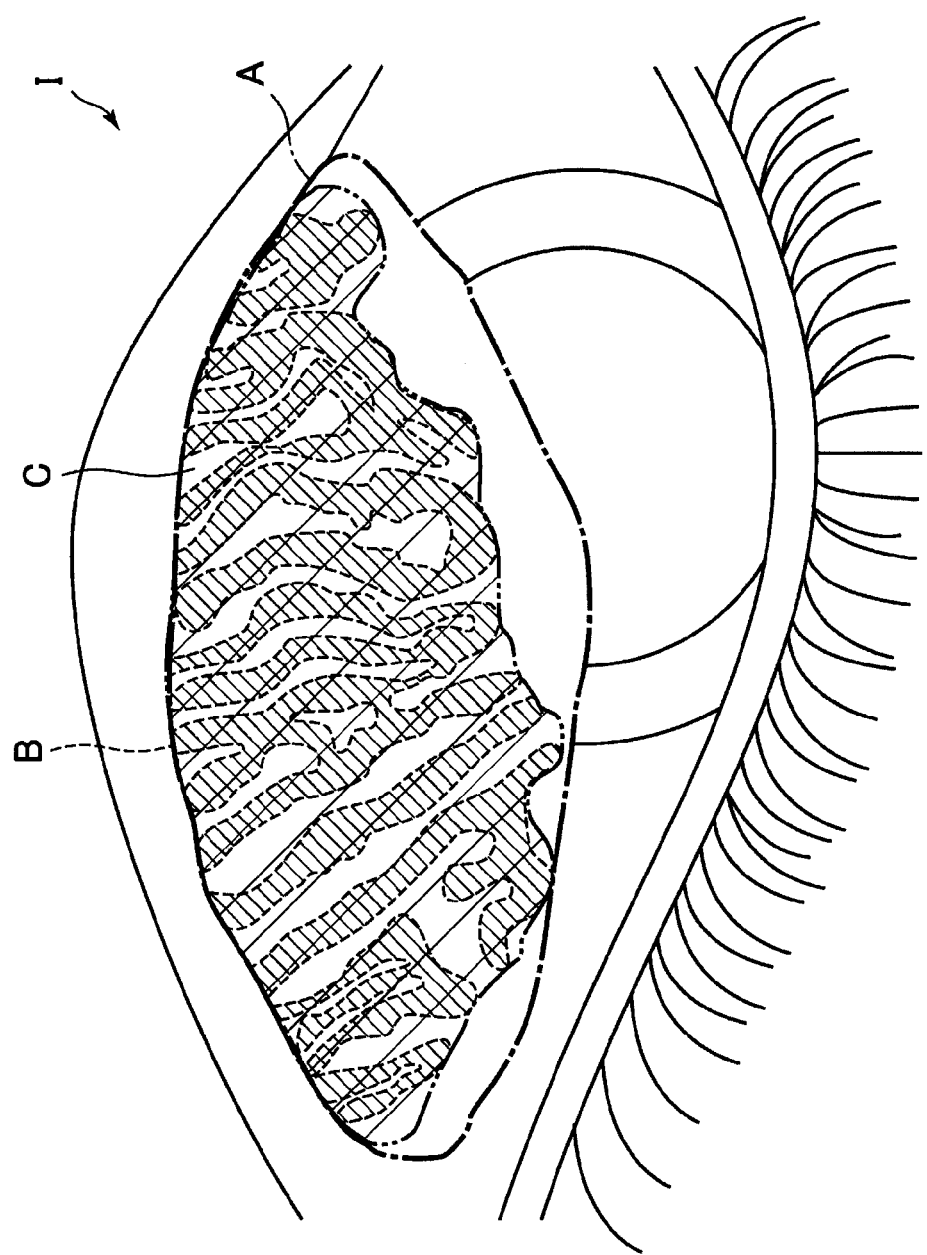
FIG. 8 is a diagram supplementing the explanation of the flowchart according to the first embodiment.
Figure 9:
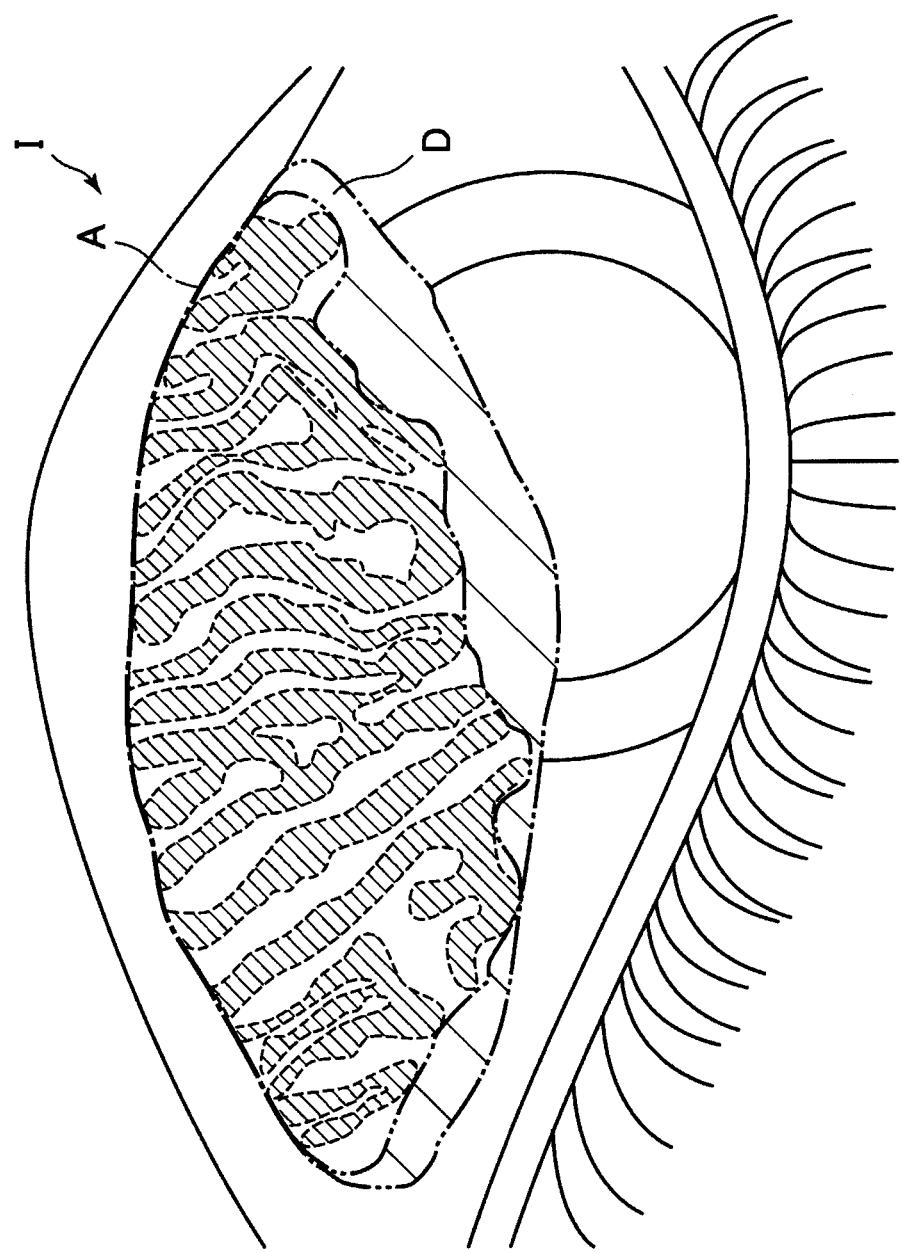
FIG. 9 is a diagram supplementing the explanation of the flowchart according to the first embodiment.

The boundary specifier 24a specifies a boundary line L that passes the vertices specified in S14, and that segments the area A being analyzed into the Meibomian-gland subareas B with the inter-Meibomian gland subareas C and into the external subareas D (S15. Refer to FIG. 7).

The boundary line L is a line that partitions the area A being analyzed into the Meibomian-gland subareas B, the inter-Meibomian gland subareas C and the external subareas D. Therefore, the subareas B+C (Refer to FIG. 8) and the subareas D (Refer to FIG. 9) are specified by specifying the boundary line L. It should be noted that the Inter-Meibomian gland subareas C are areas that are surrounded by the boundary line L, the adjacent Meibomian-gland subareas B, and the periphery of the area A being analyzed. Accordingly, the specification of the Meibomian-gland subareas B, the boundary line L, and the external subareas D results in the specification of the inter-Meibomian gland subareas C.

The occupancy calculator 24b calculates surface areas, respectively, for the area A being analyzed, the Meibomian-gland subareas B, and the inter-Meibomian gland subareas C. Then, the occupancy calculator 24b divides the sum of the surface area of the Meibomian-gland subareas B and the surface area of the inter-Meibomian gland subareas C by the surface area of the area A being analyzed, calculating an occupancy ratio O as distribution information (S16).

The determiner 24c compares the occupancy ratio O calculated in S16 with the standard occupancy ratio O' stored in the storage 3, thereby determining the existence or nonexistence of abnormality in the Meibomian glands (S17).

The display controller 25 displays, on the display 41, the photographed image I selected at S11, the processed image I' obtained by processing the photographed image I, and analysis results, for example, the result of the determination in S17 (S18. Refer to FIG. 10). It should be noted the processed image I' is generated at any of the stages after S13 by the microprocessor 2.

FIG. 10 shows an example of presentation on the display 41. The display screen 100 includes a processed image display section 101, a photographed image display section 102, and an information display section 103. In the processed image display section 101, the processed image I is displayed. In the photographed image display section 102, the photographed image I is displayed. In the information display section 103, various kinds of information are displayed. These information include a patient ID, distribution information (e.g., numerical value for the occupancy ratio O), standard information (e.g., numerical value for the standard occupancy ratio O'), and icons (GUI items) for instructional operations.

It should be noted it is not necessary to provide on the display 41 all of the processed image display section 101, the photographed image display section 102, and the information display section 103. For example, in the case of displaying only the photographed image I and the processed image I', the processed image display section 101 and the photographed image display section 102 should be provided. Furthermore, the display mode is not be restricted to the format shown in FIG. 10. It is also possible that, for example, the processed image display section 101 and the photographed image display section 102 are arranged laterally next to each other, or the photographed image display section 102 is provided in the upper part of the display screen 100 while the processed image display section 101 is provided in the lower part. Furthermore, if the system is configured with a plurality of displays 41, then the photographed image I, the processed image I', and a various kinds of information may be displayed on different displays 41.

It is also possible to configure to be capable of confirming the distribution information of the Meibomian glands in a photographed image data in real time, by sending photographed image data acquired by the ophthalmologic apparatus 6 to the ophthalmological image analyzer 1 as it is, and by carrying out the above-mentioned processing. Moreover, if the distribution information is stored in the storage 3 in connection with the patient ID, then it can be used, for example, for comparison in the future examination.

<Operations and Effects>

The operations and effects of the ophthalmological image analyzer 1 according to this embodiment are now described.

The ophthalmological image analyzer 1 comprises a designator 22, an extractor 23, and a calculator 24. The designator 22 designates an area A to be analyzed for a photographed palpebral image I of an eye. The extractor 23 extracts Meibomian-gland subareas B that indicate Meibomian glands in the palpebra, on the basis of the luminance value of each pixel in the area A being analyzed specified by the designator 22. The calculator 24 obtains distribution information of the Meibomian glands in the area A being analyzed, on the basis of the Meibomian-gland subareas B.

Therefore, according to the ophthalmological image analyzer 1, the analysis of the photographed image I can provide objective information about the state of distribution of Meibomian glands. This, accordingly, can be an assisting technology in diagnosing the state of Meibomian glands.

The ophthalmological image analyzer 1 further comprises a storage 3. The storage 3 stores standard information that indicates a standard state of distribution of the Meibomian glands in normal eyes. The calculator 24 comprises a determiner 24c, which determines whether there is abnormality in the Meibomian glands, on the basis of the distribution information and the standard information. Particularly in this embodiment, the calculator 24 comprises a boundary specifier 24a and an occupancy calculator 24b. The boundary specifier 24a specifies vertices for Meibomian-gland subareas B, and specifies, based on the specified vertices, a boundary line L that partitions the area A being analyzed into the Meibomian-gland subareas B with their inter-Meibomian gland subareas C and into the external subareas D. The occupancy calculator 24b divides the sum of the surface area of the Meibomian-gland subareas B and the surface area of the inter-Meibomian gland subareas C by the surface area of the area A being analyzed, calculating the quotient, which is an occupancy ratio O as distribution information.

Therefore, according to the ophthalmological image analyzer 1, objective information (whether normal or abnormal, and a possible cause if abnormal) about the state of distribution of the Meibomian glands can be provided on the basis of the occupancy ratio O from the photographed image I. Accordingly, it is possible to assist diagnosis of Meibomian glands.

The ophthalmological image analyzer 1 comprises a display 41 and a display controller 25. The display controller 25 displays the photographed image I, and the processed image I' which indicates the Meibomian-gland subareas B extracted by the extractor 23, side by side on the display 41. Furthermore, the display controller 25 can also display the distribution information together with the photographed image I and the processed image I' on the display 41 side by side.

Therefore, the ophthalmological image analyzer 1 can provide the photographed image and the objective information about the state of distribution of the Meibomian glands on one screen. This can be, for example, an improvement in the efficiency of conducting the diagnosis.

Second Embodiment

An ophthalmological image analyzer 1 according to a second embodiment is described with reference to FIG. 11 and FIG. 12. It should be noted that description may be omitted for the parts that are common with the first embodiment.

Figure 11:
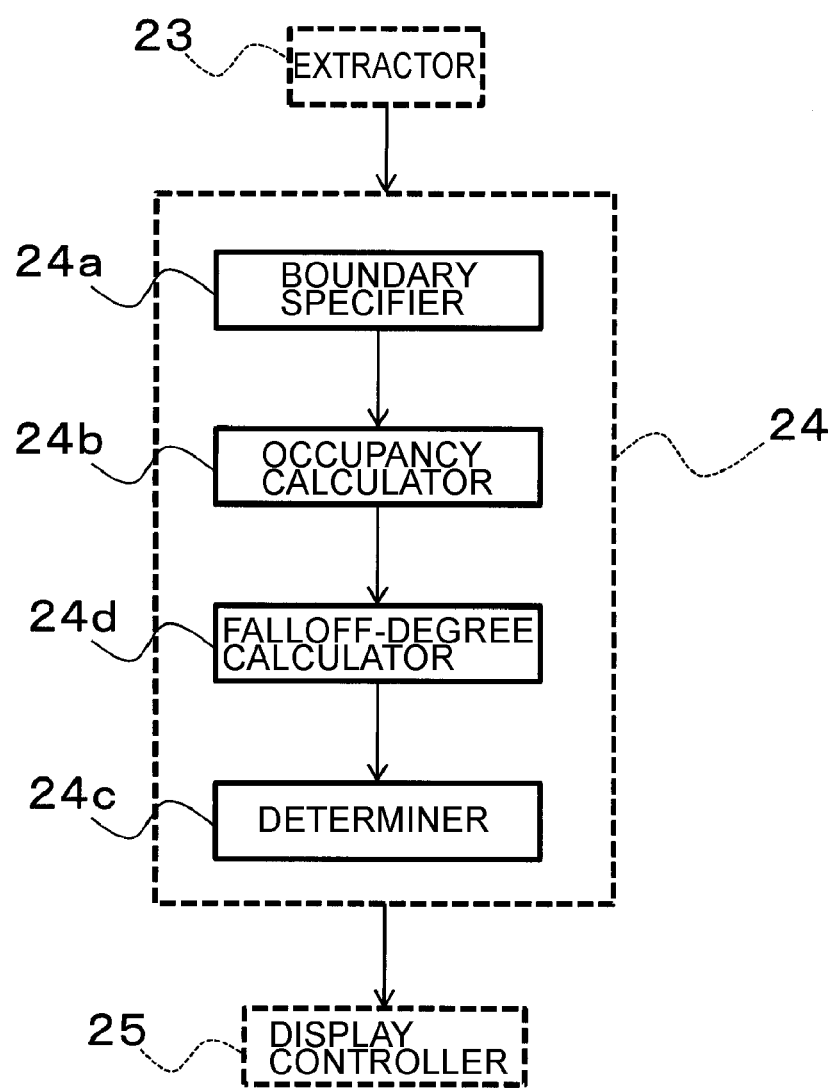
FIG. 11 is a block diagram illustrating a configuration of the calculator in the ophthalmological image analyzer according to the second embodiment.
Figure 12:
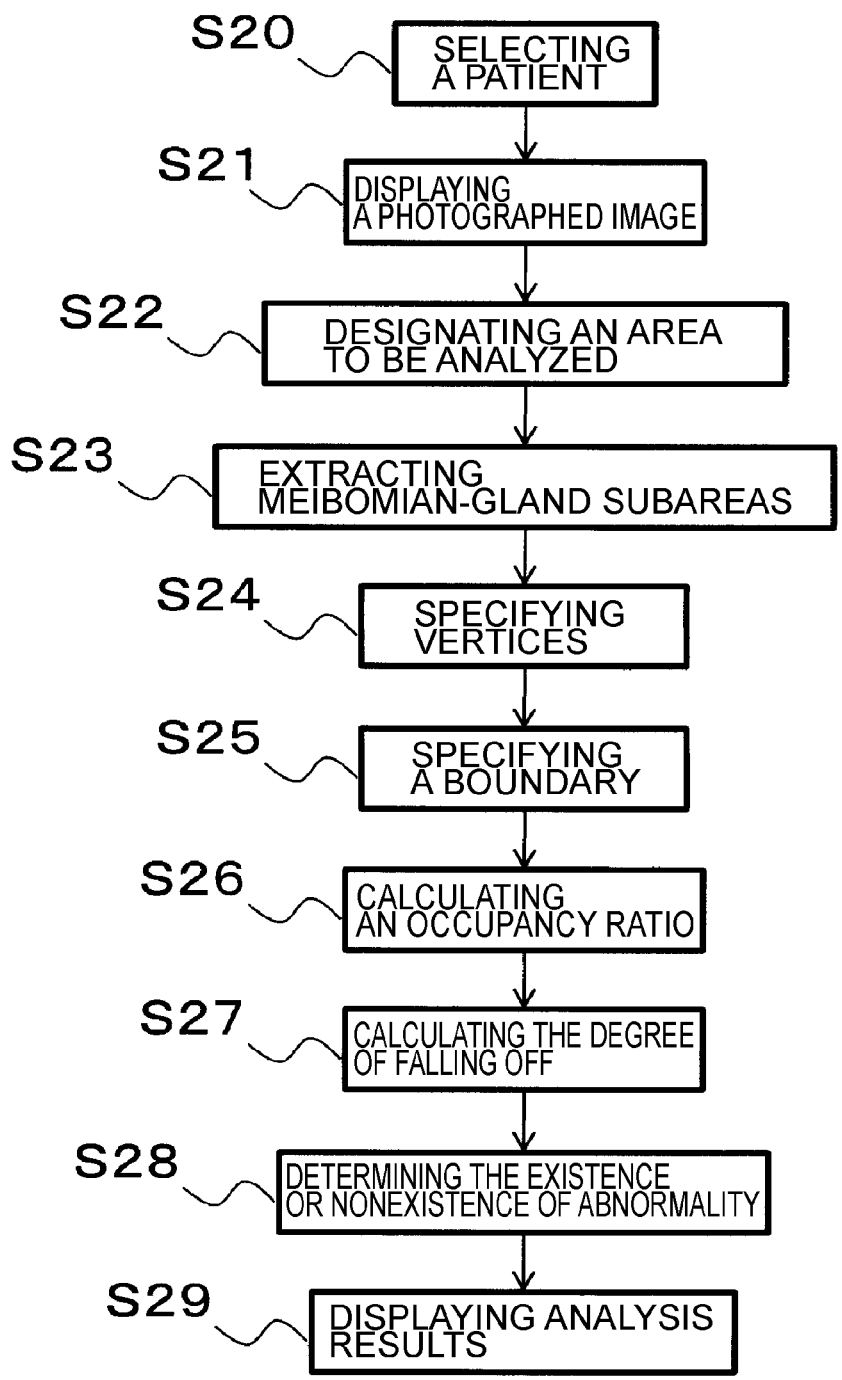
FIG. 12 is a flowchart illustrating an action of the ophthalmological image analyzer according to the second embodiment.

As shown in FIG. 11, in this embodiment, the calculator 24 is configured to include a falloff-degree calculator 24d in addition to the boundary specifier 24a, the occupancy calculator 24b, and the determiner 24c which are similar to those in the first embodiment.

The falloff-degree calculator 24d executes a process of calculating the degree of falling off of Meibomian glands. The "degree of falling off" is a parameter that indicates how much Meibomian glands have fallen off (or decreased) in contrast with Meibomian glands of normal eyes. The degree of falling off can be calculated, for example, on the basis of the occupancy ratio of Meibomian glands. In this embodiment, the degree of falling off corresponds to the distribution information.

The following describes an example of method for calculating the degree of falling off. The falloff-degree calculator 24d receives the value of the occupancy ratio calculated by the occupancy calculator 24b and the value of the standard occupancy ratio stored in the storage 3. The falloff-degree calculator 24d calculates the degree of falling off by subtracting the standard occupancy ratio from the occupancy ratio calculated by the occupancy calculator 24b.

The determiner 24c in this embodiment reads out a threshold value from the storage 3 and compares it with the degree of falling off which has been calculated by the falloff-degree calculator 24d.

This threshold value is a value used for the determination of whether the degree of falling off calculated by the falloff-degree calculator 24d is within in a normal range. The threshold value is stored in the storage 3 in advance. Instead, it can be designated for each photographed image, for example, by using the operation part 42. The threshold value is a value obtained clinically from photographed images etc. It is desirable that the threshold value be a statistical value like a mean, a median, a mode, or a standard deviation.

If the degree of falling off is larger than the threshold value, then the determiner determines that the degree of falling off is larger than that of normal eyes, meaning that there is abnormality. This determination result is displayed on the display 41 by the determiner 24c as a numerical value or a message. Instead, it is also possible that the determiner 24c causes the output unit 5 to output the determination result.

<Actions>

Now, actions taken by the ophthalmological image analyzer 1 according to this embodiment are described with reference to FIG. 12. It should be noted that the actions from S20 to S26 correspond to those from S10 to S16 in the first embodiment.

At first, the examiner selects a desired patient in the list of patients displayed on the display 41, for example, by using the operation part 42 (S20). The microprocessor 2 displays a list of photographed palpebral image data sets that correspond to the selected patient on the display 41.

The examiner selects a photographed image I for analysis of Meibomian-gland subareas from the list of sets of photographed image data. The image acquirer 21 reads out the photographed image I selected in S20, from the storage 3 and displays it on the display 41 (S21).

For the photographed image I displayed in S21, the designator 22 designates an area A to be analyzed (S22).

The extractor 23 extracts Meibomian-gland subareas B on the basis of the luminance value of each pixel in the area A being analyzed which is designated in S22 (S23).

For the Meibomian-gland subareas B extracted in S23, the boundary specifier 24a specifies the vertices of the Meibomian-gland subareas B (S24).

The boundary specifier 24a then specifies a boundary line L that passes the vertices specified in S24, and that partitions the area A being analyzed into the Meibomian-gland subareas B with their inter-Meibomian gland subareas C and into an external subareas D (S25).

The occupancy calculator 24b calculates, respectively, surface areas for the area A being analyzed, the Meibomian-gland subareas B, and the inter-Meibomian gland subareas C. Then, the occupancy calculator 24b calculates an occupancy ratio O by dividing the sum of the surface area of the Meibomian-gland subareas B and the surface area of the inter-Meibomian gland subareas C by the surface area of the area A being analyzed (S26).

The falloff-degree calculator 24d receives the occupancy ratio O calculated in S26 and the standard occupancy ratio O' stored in the storage 3. The falloff-degree calculator 24d calculates the degree of falling off by subtracting the standard occupancy ratio O' from the occupancy ratio O (S27).

The determiner 24c determines the existence or nonexistence of abnormality of the Meibomian glands by comparing the degree of falling off calculated in S27 with the threshold value stored in the storage 3 (S28).

The display controller 25 displays, on the display 41, the photographed image selected in S21, the processed image I' which is obtained by applying a process to the photographed image, and the analysis results such as the result of the determination in S28. (S29).

<Operations and Effects>

Now, the description concerns the operations and effects of the ophthalmological image analyzer 1 according to this embodiment.

The storage 3 of the ophthalmological image analyzer 1 stores a predetermined threshold value and a standard occupancy ratio which is the ratio of the Meibomian-gland subareas and the inter-Meibomian gland subareas (i.e., subareas between the Meibomian-gland subareas) occupying the area being analyzed of normal eyes. The calculator 24 of the ophthalmological image analyzer 1 comprises a boundary specifier 24a, an occupancy calculator 24b, a falloff-degree calculator 24d, and a determiner 24c. The boundary specifier 24a specifies vertices for the Meibomian-gland subareas, and then, based on the vertices, defines a boundary that segments the area being analyzed into the Meibomian-gland subareas and inter-Meibomian gland subareas (i.e., subareas between the Meibomian-gland subareas) and into the other remaining external subareas. The occupancy calculator 24b divides the sum of the surface area of the Meibomian-gland subareas and the surface area of the inter-Meibomian gland subareas by the surface area of the area being analyzed, calculating the quotient as the occupancy ratio. The falloff-degree calculator 24d calculates the degree of falling off of the Meibomian glands relative to normal eyes as distribution information by obtaining a difference between the occupancy ratio calculated by the occupancy calculator 24b and the standard occupancy ratio. The determiner 24c determines the existence or nonexistence of abnormality in the Meibomian glands on the basis of the degree of falling off calculated by the falloff-degree calculator 24d and the threshold value.

Therefore, according to the ophthalmological image analyzer 1, objective information about the state of distribution of the Meibomian glands can be provided on the basis of the degree of falling off of the Meibomian glands. Accordingly, it can assist diagnosis of Meibomian glands.

Modified Examples of the First and Second Embodiments

As causes of abnormality of Meibomian glands, occlusive MGD and allergic conjunctivitis are known in addition to wearing of contact lenses which has been mentioned above. Therefore, it is possible to assist the diagnosis of Meibomian glands by specifying the cause of abnormality of Meibomian glands on the basis of distribution information.

Modified Example 1

Here, in the case of an abnormality in the Meibomian glands due to occlusive MGD, it is known that the shape of the boundary between the Meibomian-gland subareas with the inter-Meibomian gland subareas and the external subareas looks like saw-teeth (i.e., the shape in which some of the Meibomian glands have become extremely shorter than others).

Accordingly, the calculator 24 in this modified example obtains, as the distribution information, shape information that indicates the shape of the boundary specified by the boundary specifier 24a. The shape information can be obtained by determining, for example, how far the coordinate values of the vertices of adjacent Meibomian glands deviate from one another (e.g., how far the coordinate values deviate from one another in the y direction).

The determiner 24c can determine the existence or nonexistence of abnormality in the Meibomian glands on the basis of the shape information of the boundary and the standard information stored in the storage 3. The "standard information" here can be obtained by determining how far the coordinate values of the vertices of adjacent Meibomian glands deviate from one another (e.g., how far the coordinate values deviate from one another in the y direction) in normal eyes.

According to this modified example, objective information about the state of distribution of the Meibomian glands can be provided on the basis of the shape information of the boundary. Since a cause of abnormality in the Meibomian glands can be specified in this way, this modified example can assist the diagnosis.

Modified Example 2

On the other hand, in the case of an abnormality in the Meibomian glands due to allergic conjunctivitis, it is known that the Meibomian glands have large bends.

The calculator 24 in this modified example performs a process that obtains the degree of bending of the Meibomian glands as distribution information, on the basis of the shape of the Meibomian-gland subareas extracted by the extractor 23. The term "degree of bending" is a parameter that indicates how much each Meibomian gland is bent. The degree of bending can be expressed, for example, as a value that indicates how far the bend of the Meibomian gland is away from a reference straight line.

It is possible for the calculator 24 to calculate the degree of bending by derives the surface area surrounded by a curve that indicates the shape of the Meibomian gland and by a straight line that passes two arbitrary points in this curve (e.g., both end points of the curve). In this case, the larger the surface area is, the greater the bend of the Meibomian gland is. On the basis of the degree of bending, it is possible to determine the existence or nonexistence of abnormality in the Meibomian glands, and the degree of the abnormality if there is.

Instead, it is also possible to calculate the degree of bending by executing differential processing on the curve that represent the periphery of the Meibomian-gland subarea or on the curve obtained by thinning the Meibomian-gland subarea. In this case, the degree of bending can be, for example, the number of bent parts (inflection points) of the Meibomian-gland subarea or the curvatures at the inflection points. The same technique as mentioned in the first embodiment can be applied to the calculation of the inflection points here.

For example, the calculator 24 can calculate the curvature at an inflection point by calculating the radius for the circle that is tangent to the curve that represents the shape of the Meibomian gland at the inflection point. If the curvature is small, it means that the degree of bending of the Meibomian-gland subarea is small. On the contrary, if the curvature is large, then it means that the degree of bending of the Meibomian-gland subarea is large. For example, it can be so arranged that if the curvature is larger than a predetermined threshold value, then it can be said that the Meibomian-gland subarea has a large bend, in other words, there is abnormality in the Meibomian gland.

The calculator 24 calculates the degree of bending of each of the Meibomian-gland subareas, and on the basis of the statistical value of the calculated degrees of bending and the standard information stored in the storage 3, the determiner 24c determines the existence or nonexistence of abnormality in the Meibomian glands. It should be noted that the "standard information" here is the degree of bending of Meibomian glands in normal eyes. It is desirable that the standard information be a mean, a median, a mode, a standard deviation, etc. of the degrees of bending calculated for the Meibomian glands in a plurality of normal eyes. Furthermore, the statistical value of the degrees of bending may be, for example, a mean, a median, a mode, a standard deviation, a sum of degrees of bending, or a maximum or minimum value for the degrees of bending.

According to this modified example, objective information about the state of distribution of the Meibomian glands can be provided on the basis of the degree of bending to the examiner. Since the cause of abnormality in the Meibomian glands is specified in this way, this modified example can assist the diagnosis.

Third Embodiment

An ophthalmological image analyzer 1 according to a third embodiment is described with reference to FIG. 13 and FIG. 14. Here, description may be omitted for the parts that are similar to the first and second embodiments.

As described above, various types of information can be considered as distribution information of Meibomian glands. Further diagnostic assistance can be, therefore, realized by combining these types of distribution information. Such an example is described in this embodiment.

Figure 13:
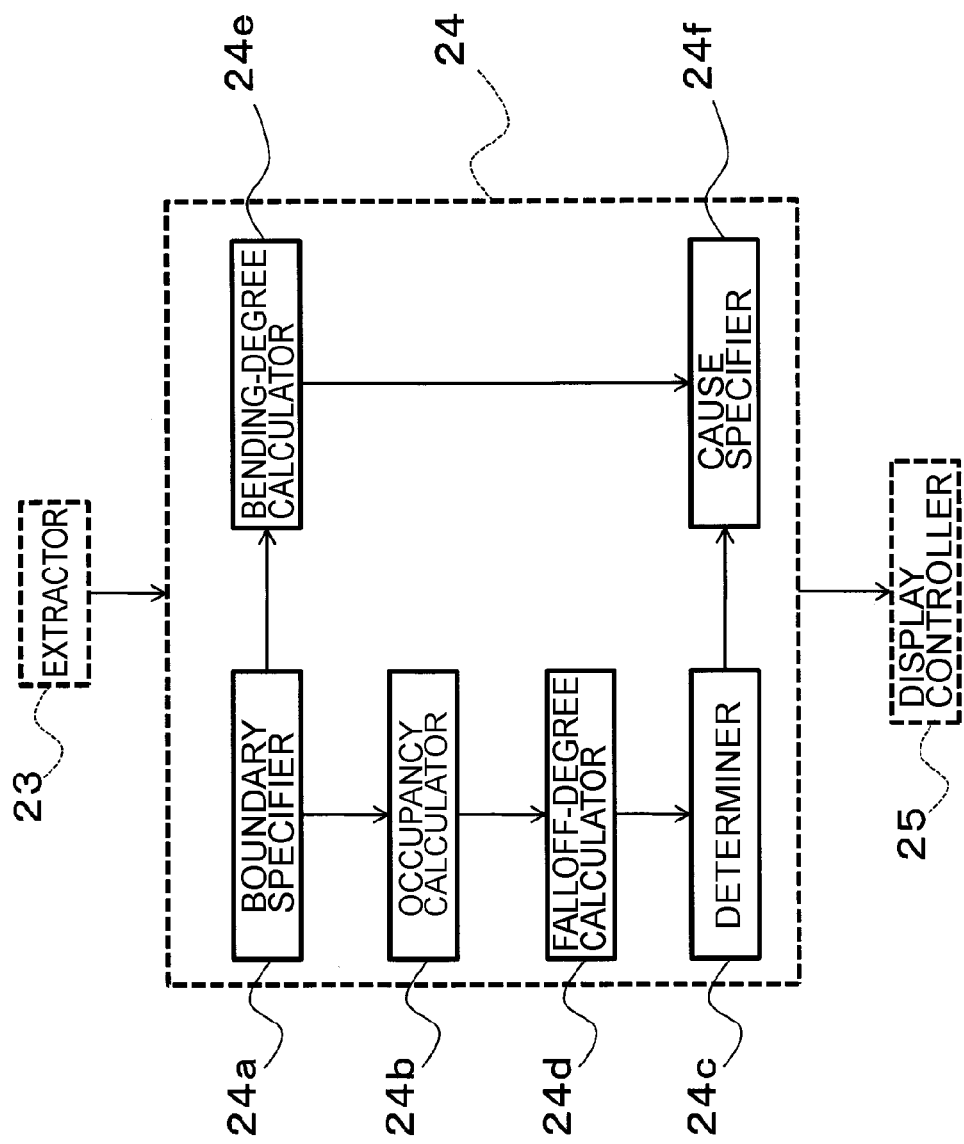
FIG. 13 is a block diagram illustrating a configuration of the calculator in the ophthalmological image analyzer according to the third embodiment.
Figure 14:
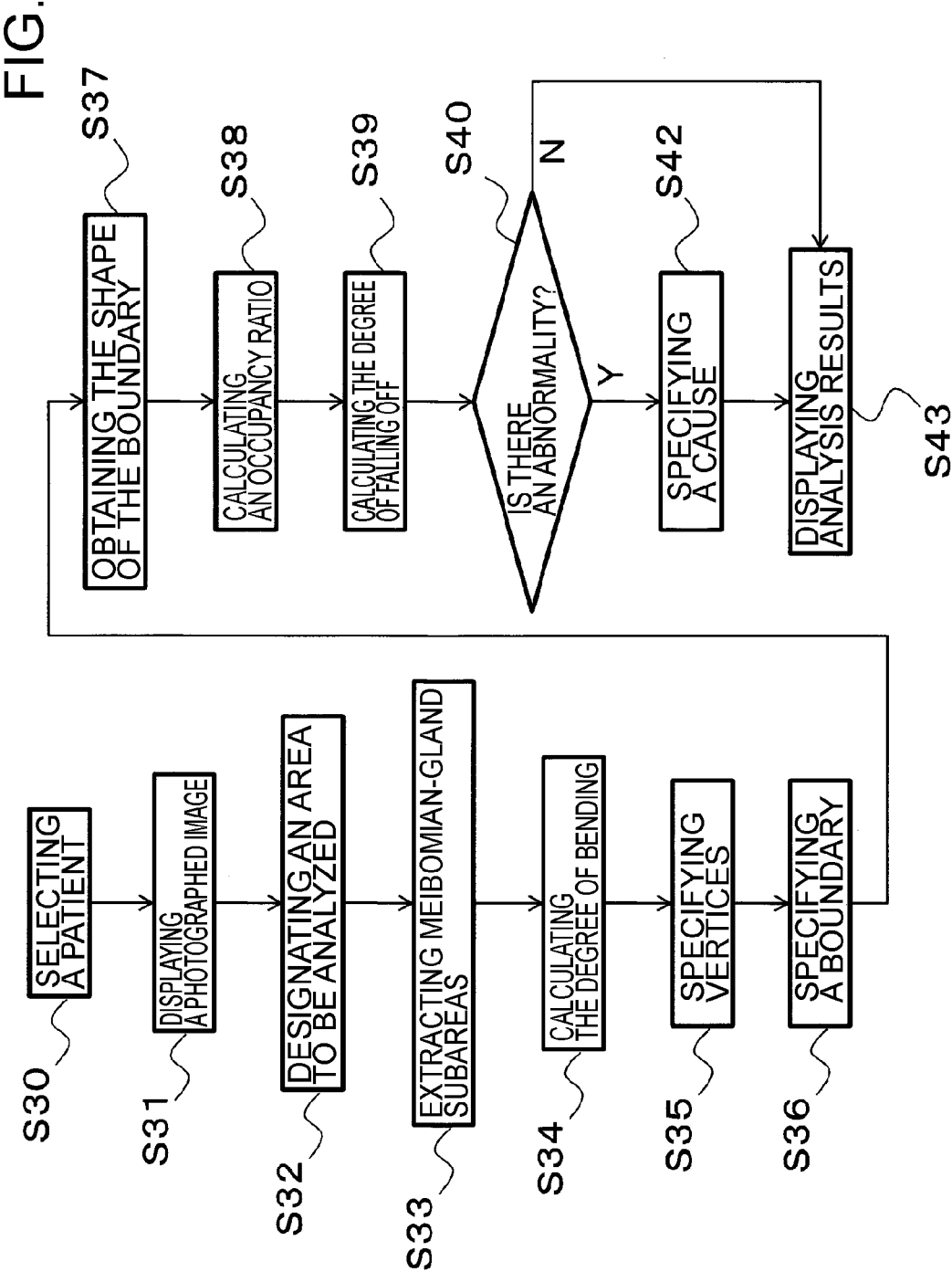
FIG. 14 is a flowchart illustrating an action of the ophthalmological image analyzer according to the third embodiment.

As shown in FIG. 13, in this embodiment, the calculator 24 is configured to include a bending-degree calculator 24e and a cause specifier 24f in addition to a boundary specifier 24a, an occupancy calculator 24b, a determiner 24c, and a falloff-degree calculator 24d which are similar to those in the second embodiment.

The bending-degree calculator 24e calculates the degree of bending of the Meibomian glands as distribution information on the basis of the shape of the Meibomian-gland subareas extracted by the extractor 23. The calculation of the degree of bending can be executed by using the same technique as in modified example 2.

When the determiner 24c determines that there is an abnormality in the Meibomian glands, the cause specifier 24f specifies a possible cause (a candidate of its cause) for the abnormality in the Meibomian glands on the basis of the shape information that indicates the shape of the boundary specified by the boundary specifier 24a and/or the degree of bending.

<Actions>

Now, actions taken by the ophthalmological image analyzer 1 according to this embodiment are described with reference to FIG. 14. It should be noted that actions S30 through S33 correspond to those S10 through S13 in the first embodiment (S20 through S23 in the second embodiment).

At first, the examiner selects a desired patient, for example, in the list of patients displayed on the display 41 by using the operation part 42 etc. (S30). The microprocessor 2 displays, on the display 4, a list of photographed palpebral image data sets that correspond the selected patient.

The examiner then selects a photographed image I for analysis of Meibomian-gland subareas from the list of sets of photographed image data. The image acquirer 21 reads out the photographed image I selected in S30 from the storage 3 and displays it on the display 4 (S31).

For the photographed image I displayed in S31, the designator 22 designates an area A to be analyzed (S32).

The extractor 23 extracts Meibomian-gland subareas B on the basis of the luminance value of each pixel in the area A being analyzed specified in S32 (S33).

In addition, the bending-degree calculator 24e calculates as distribution information the degree of bending of the Meibomian glands on the basis of the shape of the Meibomian-gland subareas B extracted in S33 (S34). The information representing the calculated degree of bending is stored in the storage 3.

For the Meibomian-gland subareas B extracted in S33, the boundary specifier 24a specifies the vertices of the Meibomian-gland subareas B (S35).

The boundary specifier 24a then specifies a boundary line L that passes the vertices specified in S35, and that partitions the area A being analyzed into the Meibomian-gland subareas B with the inter-Meibomian gland subareas C and into the external subareas D (S36).

Furthermore, the calculator 24 obtains as distribution information the shape information that indicates the shape of the boundary line L specified in S36 (S37). The calculation of the shape information of the boundary can be executed by using the same technique as in modified example 1. The obtained shape information of the boundary is stored in the storage 3.

The occupancy calculator 24b calculates, respectively, surface areas for the area A being analyzed, the Meibomian-gland subareas B, and the inter-Meibomian gland subareas C. Then, the occupancy calculator 24b calculates an occupancy ratio O by dividing the sum of the surface area of the Meibomian-gland subareas B and the surface area of the inter-Meibomian gland subareas C by the surface area of the area A being analyzed (S38).

The falloff-degree calculator 24d receives the occupancy ratio O calculated in S38 and the standard occupancy ratio O' stored in the storage 3. The falloff-degree calculator 24d calculates the degree of falling off by subtracting the occupancy ratio O from the standard occupancy ratio O' (S39).

The determiner 24c determines the existence or nonexistence of abnormality in the Meibomian glands by comparing the degree of falling off calculated in S39 with the threshold value stored in the storage 3 (S40).

Here, if the determiner 24c determines that there is abnormality in the Meibomian glands (in the case of Y at S40), the cause specifier 24f specifies a possible cause for the abnormality in the Meibomian glands on the basis of the degree of bending calculated in S34 and the shape information of the boundary line L obtained in S37 (S42). As a specific example, the calculator 24 specifies a possible cause for the abnormality in the Meibomian glands by referring to table information. The table information is stored in the storage 3 or the like. In the table information, a range for the degrees of bending (range showing whether it is within standard information) and a range for the shape information of the boundary (range showing whether it is within standard information) are associated to causes of abnormality. It is possible to specify a cause of abnormality in accordance with the ranges to which the degree of bending calculated in S34 and the shape information of the boundary line L calculated at S37 belongs, respectively. It should be noted that causes of abnormality are, for example, "allergic conjunctivitis", "contact lenses", etc.

Based on the table information, for example, if it is determined that the degree of bending is larger than the standard information and that the shape information of the boundary line L is similar to the standard information, then the calculator 24 specifies that the abnormality in the Meibomian glands is due to allergic conjunctivitis.

Then, the display controller 25 displays, on the display 41, the photographed image I selected in S31, the processed image I' obtained by processing the photographed image, and the cause of the abnormality in the Meibomian glands specified in S42 (S43).

On the other hand, if the determiner 24c has determined that there is no abnormality in the Meibomian glands (in the case of N at S40), the display controller 25 displays, on the display 41, the photographed image I selected at S31, the processed image I' obtained by processing the photographed image, and the determination result that there is no abnormality in the Meibomian glands obtained in S40 (S43).

It should be noted that parameters used for specifying a possible cause for the abnormality in the Meibomian glands in S42 can be set arbitrarily in accordance with causes for abnormalities to be determined. For example, at least either the degree of bending or the shape information of the boundary line L may be used as the parameter. Instead, other parameters such as the occupancy ratio or the degree of falling off can be considered.

<Operations and Effects>

Now, the description concerns the operations and effects of the ophthalmological image analyzer 1 according to this embodiment.

The calculator 24 of the ophthalmological image analyzer 1 comprises a bending-degree calculator 24e and a cause specifier 24f. The bending-degree calculator 24e calculates as distribution information the degree of bending for the Meibomian glands on the basis of the shape of the Meibomian-gland subareas extracted by the extractor 23. The cause specifier 24f, in response to the result of the determination by the determiner 24c that there is an abnormality in the Meibomian glands, specifies a possible cause for the abnormality in the Meibomian glands on the basis of the shape information that indicates the shape of the boundary specified by the boundary specifier 24a and/or the degree of bending.

As a result, if the Meibomian glands are in abnormal state, the analyzer can provide information that is used for specifying the cause of the abnormality. Accordingly, the analyzer can assist the diagnosis of Meibomian glands or the like.

Modified Examples Common to the First Through Third Embodiments

The contents described above are merely examples of configuration that realizes the present invention. A person who intends to implement the present invention can perform any modification within the scope of the present invention.

Modified Example 3

Figure 15:
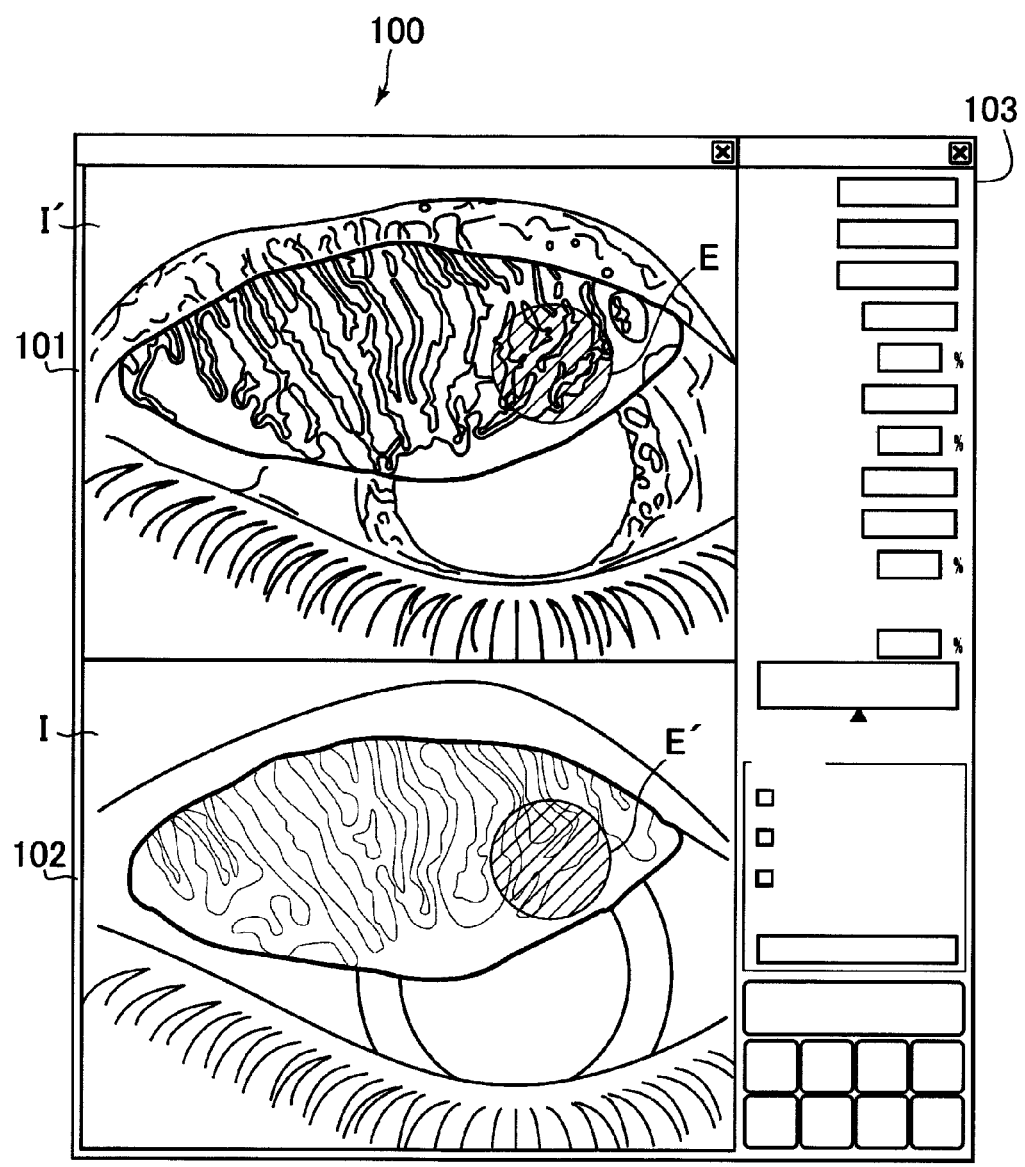
FIG. 15 is a diagram illustrating a display screen on the display in the ophthalmological image analyzer according to the modified example 3.

When an instruction is executed on one of the photographed image and the processed image by using the operation part 42, the display controller 25 can reflect the result of this instruction on the other image. As a specific example, when an area E to be analyzed is designated on the processed image I' as shown in FIG. 15, the display controller 25 causes to display the part E' that corresponds to the area E to be analyzed on the photographed image I. The extractor 23 and the calculator 24 can execute the same analysis processing as in the above mentioned embodiment on the area E being analyzed and obtain distribution information of the Meibomian glands. The processed image I' provides easier recognition of the Meibomian-gland subareas than the photographed image, and therefore it can help the examiner to easily recognize where, in the photographed image, the Meibomian-gland subareas shown in the processed image I' exist. In the other way around, the result of an operation done on the photographed image I can be reflected on the processed image I' in such a way that the part in the photographed image I that is hard to recognize can be easily identified in the processed image I'. Remember that the processed image I' is created based on the photographed image I. It is, therefore, not necessary to carry out position matching between the processed image I' and the photographed image I that are displayed on the display 41.

Modified Example 4

The distribution information is not limited to those types mentioned above. For example, the difference (contrast) in luminance value between the Meibomian-gland subareas and the other subareas in the area being analyzed, the widths of the Meibomian-gland subareas, etc. can be used as the distribution information. On the basis of these types of distribution information, the determiner 24c can determine the existence or nonexistence of abnormality in the Meibomian glands by similar threshold processing to the above-mentioned embodiments. In addition, the distribution information mentioned here can be applied as one type of distribution information that is used for specifying a possible cause for the abnormality in the Meibomian glands in the third embodiment.

<About the Programs>

The program of this embodiment is used for controlling a computer that analyzes a photographed palpebral image of an eye in order to execute a method of ophthalmological image analysis.

Specifically, the program causes the computer to function as the following parts: (1) designator 22, which is configured to designate an area to be analyzed in a photographed image, the area including Meibomian glands; (2) extractor 23, which is configured to extract Meibomian-gland subareas that indicate Meibomian glands in the palpebra, on the basis of the luminance value of each pixel in the area being analyzed; and (3) calculator 24, which is configured to obtain distribution information of Meibomian glands in the area being analyzed, on the basis of the Meibomian-gland subareas.

According to the method of ophthalmological image analysis realized by such a program, a computer can provide objective information about the state of distribution of the Meibomian glands by analyzing a photographed image I. The method, therefore, can assist the diagnosis of the Meibomian glands or the like.

Furthermore, the program according to the present invention can be stored in arbitrary storage media that are readable by computer-driven devices. Such storage media include, for example, optical discs, magneto-optical disks (CD-ROM, DVD-RAM, DVD-ROM, MO, etc.), and magnetic storages (hard disk drives, Floppy (registered trademark) disks, ZIP disks, etc.). The program can be stored in such a storage device as a hard disk drive or a memory device. Also, it is possible to send the program through networks like the Internet and a LAN.

EXPLANATION OF THE SYMBOLS 1 ophthalmological image analyzer
2 microprocessor
3 storage
4 user interface
5 output unit
6 ophthalmologic apparatus
21 image acquirer
22 designator
23 extractor
24 calculator
24a boundary specifier
24b occupancy calculator
24c determiner
25 display controller
41 display
42 operation part

What is claimed is:

1. A method of ophthalmological image analysis, comprising:
 a step of designating an area to be analyzed in a photographed image of an eyelid of an eye;
 a step of extracting Meibomian-gland subareas that represent Meibomian glands in the eyelid, on the basis of the luminance value of each pixel in the area being analyzed;
 a step of specifying vertices for the Meibomian-gland subareas, and on the basis of the vertices, specifying a boundary that divides the area being analyzed into the Meibomian-gland subareas with the inter-Meibomian gland subareas, which are subareas that exist between the Meibomian-gland subareas, and into the other remaining external subareas; and
 a step of dividing the sum of the surface area of the Meibomian-gland subareas and the surface area of the inter-Meibomian gland subareas by the surface area of the area being analyzed, calculating the quotient, which represents occupancy ratio as distribution information of Meibomian glands in the area being analyzed.

2. A method of ophthalmological image analysis, comprising:
 a step of designating an area to be analyzed in a photographed image of an eyelid of an eye;
 a step of extracting Meibomian-gland subareas that represent Meibomian glands in the eyelid, on the basis of the luminance value of each pixel in the area being analyzed;
 a step of specifying vertices for the Meibomian-gland subareas, and on the basis of the vertices, specify a boundary that divides the area being analyzed into the Meibomian-gland subareas with the inter-Meibomian gland subareas, which are subareas that exist between the Meibomian-gland subareas, and into the other remaining external subareas; and
 a step of acquiring, as distribution information of Meibomian glands in the area being analyzed, shape information that indicates the shape of the boundary.

3. A method of ophthalmological image analysis, comprising:
 a step of designating an area to be analyzed in a photographed image of an eyelid of an eye;
 a step of extracting Meibomian-gland subareas that represent Meibomian glands in the eyelid, on the basis of the luminance value of each pixel in the area being analyzed; and
 a step of acquiring, as distribution information of Meibomian glands in the area being analyzed, a degree of bending for the Meibomian glands, on the basis of the shape of the Meibomian-gland subareas.

4. A method of ophthalmological image analysis, comprising:
 a step of storing a predetermined threshold value and a standard occupancy ratio, which is the ratio of Meibomian-gland subareas and inter-Meibomian gland subareas, which are subareas that exist between the Meibomian-gland subareas, occupying an area being analyzed of a normal eye;
 a step of designating an area to be analyzed in a photographed image of an eyelid of an eye;
 a step of extracting Meibomian-gland subareas that represent Meibomian glands in the eyelid, on the basis of the luminance value of each pixel in the area being analyzed;
 a step of specifying vertices for the Meibomian-gland subareas, and on the basis of the vertices, specify a boundary that divides the area being analyzed into the Meibomian-gland subareas with the inter-Meibomian gland subareas, which are subareas that exist between the Meibomian-gland subareas, and into the other remaining external subareas;
 a step of dividing the sum of the surface area of the Meibomian-gland subareas and the surface area of the inter-Meibomian gland subareas by the surface area of the area being analyzed, calculating the quotient, which represents occupancy ratio;
 a step of acquiring, as distribution information of Meibomian glands in the area being analyzed, a degree of falling off of the Meibomian glands compared with the normal eye by calculating the difference between the occupancy ratio and the standard occupancy ratio; and
 a step of determining the existence or nonexistence of abnormality in the Meibomian glands, on the basis of the degree of falling off and the threshold value.

* * * * *